United States Patent
Fischer et al.

(10) Patent No.: US 10,188,845 B2
(45) Date of Patent: Jan. 29, 2019

(54) HEMOSTASIS VALVE ASSEMBLY

(71) Applicant: St. Jude Medical, Cardiology Division, Inc., St. Paul, MN (US)

(72) Inventors: Brian Fischer, Minneapolis, MN (US); Jennifer M. Heisel, Princeton, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 249 days.

(21) Appl. No.: 14/271,896

(22) Filed: May 7, 2014

(65) Prior Publication Data

US 2014/0343512 A1     Nov. 20, 2014

Related U.S. Application Data

(60) Provisional application No. 61/825,351, filed on May 20, 2013.

(51) Int. Cl.
| | |
|---|---|
| *A61M 39/06* | (2006.01) |
| *A61B 17/34* | (2006.01) |
| *A61B 17/00* | (2006.01) |

(52) U.S. Cl.
CPC ..... *A61M 39/0606* (2013.01); *A61B 17/3498* (2013.01); *A61M 39/06* (2013.01); *A61B 2017/00526* (2013.01); *A61B 2017/00778* (2013.01); *A61M 2039/062* (2013.01); *A61M 2039/064* (2013.01); *A61M 2039/0626* (2013.01); *A61M 2039/0653* (2013.01)

(58) Field of Classification Search
CPC .............. A61M 39/0606; A61M 39/06; A61M 2039/062; A61M 2039/064; A61M 2039/0653; A61M 2039/0626; A61B 17/3498; A61B 2017/00778; A61B 2017/00526

See application file for complete search history.

(56) References Cited

U.S. PATENT DOCUMENTS

| | | | | |
|---|---|---|---|---|
| 4,673,393 | A | * | 6/1987 | Suzuki ............. A61M 39/0606 138/89 |
| 5,114,408 | A | | 5/1992 | Fleischhaker et al. |
| 5,149,327 | A | * | 9/1992 | Oshiyama ......... A61M 39/0606 251/149.1 |

(Continued)

FOREIGN PATENT DOCUMENTS

| | | |
|---|---|---|
| EP | 2548605 A1 | 1/2013 |
| WO | 9715338 A1 | 5/1997 |

OTHER PUBLICATIONS

Definition of "intersect" Collins Dictionary, definition No. 1. Available online Oct. 20, 2016 at http://www.collinsdictionary.com/dictionary/english/intersect.*

*Primary Examiner* — Amber Stiles
(74) *Attorney, Agent, or Firm* — Armstrong Teasdale LLP

(57) ABSTRACT

A hemostasis valve assembly includes a housing and a valve member. The housing includes a central bore. The valve member is positioned within the housing and includes opposed first and second primary surfaces, a thickness, an opening, and first and second slits. The valve thickness is defined between the first and second primary surfaces. The opening is formed in the first primary surface. The first and second slits intersect each other and extend through a portion of the valve thickness. At least one of the first and second slits is accessible within the opening.

7 Claims, 21 Drawing Sheets

(56) References Cited

U.S. PATENT DOCUMENTS

| | | | |
|---|---|---|---|
| 5,167,637 A * | 12/1992 | Okada | A61M 39/0606 251/149.1 |
| 5,304,156 A | 4/1994 | Sylvanowicz et al. | |
| 2004/0127855 A1 * | 7/2004 | Core | A61M 39/0606 604/167.04 |
| 2009/0012476 A1 | 1/2009 | Catlin | |
| 2010/0063364 A1 * | 3/2010 | Bonadio | A61B 17/3423 600/208 |
| 2011/0282286 A1 | 11/2011 | Argentine | |
| 2012/0184971 A1 | 7/2012 | Zentgraf et al. | |
| 2012/0245527 A1 | 9/2012 | Stephens | |

* cited by examiner

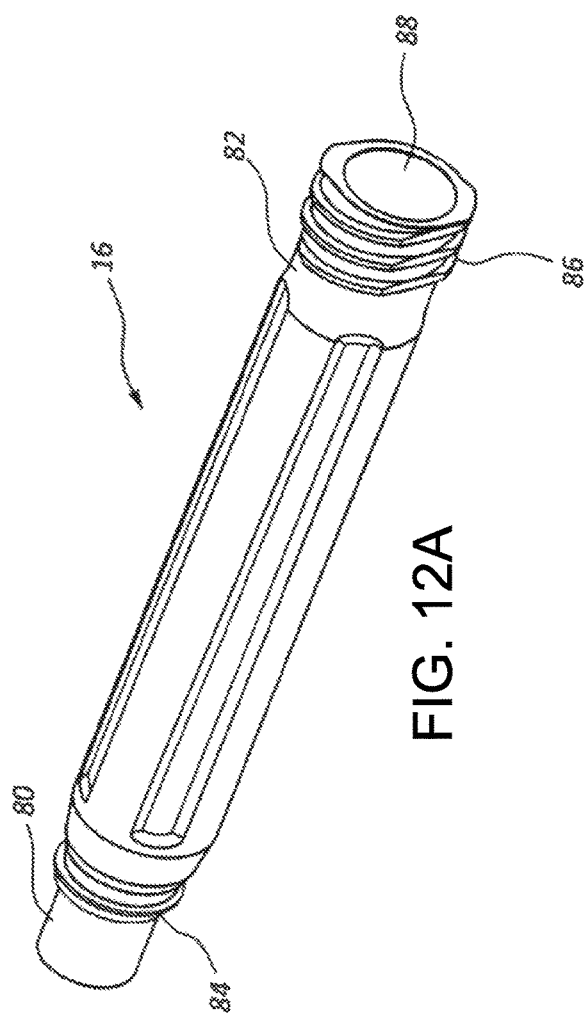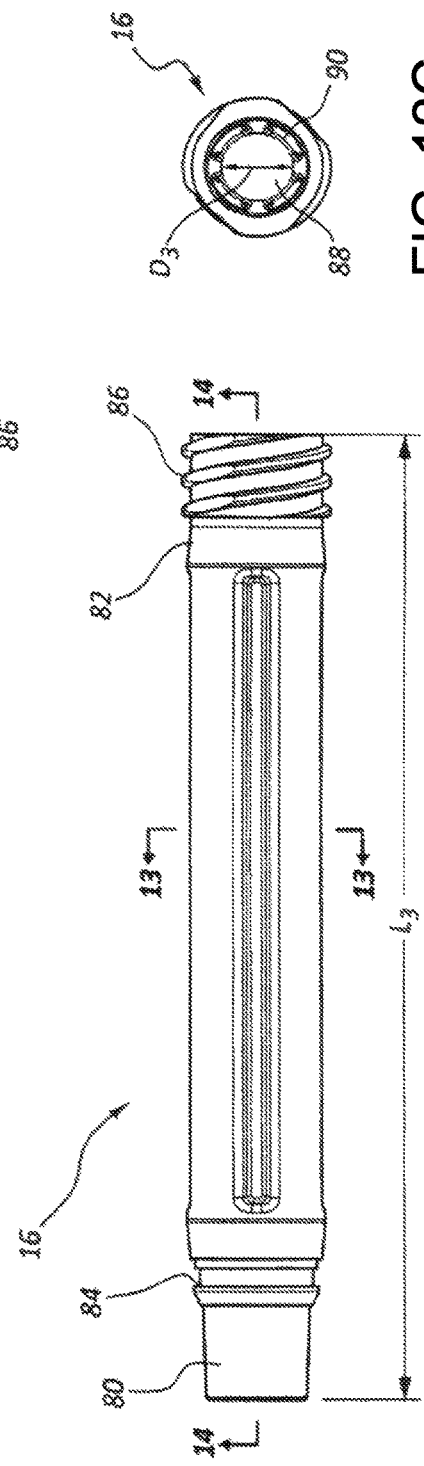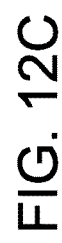

HEMOSTASIS VALVE ASSEMBLY

CROSS-REFERENCE TO RELATED APPLICATIONS

This application claims priority from U.S. Provisional Patent Application Ser. No. 61/825,351, filed on May 20, 2013, which is herein incorporated by reference in its entirety.

TECHNICAL FIELD

The present disclosure relates to introducer sheaths, and more particularly relates to introducer sheaths with hemostasis valves.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an introducer (also referred to as an introducer sheath or an insertion sheath) may be placed in the artery and thereafter instruments (e.g., catheters) may pass through the introducer to an operative position within the patient.

The introducer is typically designed to penetrate the skin and wall of a blood vessel and be positioned within the patient so that surgical implements and medical devices may be advanced and withdrawn through the introducer. In this way, even when multiple surgical implements and medical devices are used in a single procedure, there is a single placement of the introducer through the skin and vessel wall.

Introducers may include valves that prevent back flow of blood through the introducer and introduction of air into the introducer and vessel, while permitting advancement of the surgical implements and medical devices to the vessel. Introducer valves are typically categorized as passive or active. A passive valve generally relies on the deformation of a resilient sealing member by an implement or medical device that is inserted through the valve to form the desired fluid-tight seal. An active valve typically includes a mechanism that moves a sealing member into contact with the implement or medical device.

SUMMARY

One aspect of the present disclosure relates to a hemostasis valve assembly which includes a housing and a valve member. The housing includes a central bore. The valve member is positioned within the housing and includes opposed first and second primary surfaces, a thickness, an opening, and first and second slits. The valve thickness is defined between the first and second primary surfaces. The opening is formed in the first primary surface. The first and second slits intersect each other and extend through a portion of the valve thickness. At least one of the first and second slits is accessible within the opening.

Another aspect relates to a sheath assembly that includes an introducer having distal and proximal ends, a valve assembly mounted to the proximal end of the introducer, and an alignment device extending proximally from the valve assembly and having a lumen axially aligned with the valve assembly.

A further aspect relates to a sheath assembly which includes an introducer, a valve assembly, and a flow adapter. The introducer has distal and proximal ends. The valve assembly is mounted to the proximal end of the introducer. The flow adapter extends proximally from the valve assembly and includes an insertion portion extending into the valve assembly to maintain the valve assembly in an open position, and a flow controller operable to control fluid flow through the flow adapter.

Another aspect relates to a method of manufacturing a valve member. The method includes providing a resilient valve member having a perimeter and opposing first and second primary surfaces, and forming an opening in the valve member, wherein the opening has a first diameter and a first depth extending from the first primary surface toward the second primary surface. The method also includes forming a recess in the valve member, wherein the recess is arranged coaxially with the opening and has a second diameter greater than the first diameter and a second depth extending from the opening toward the second primary surface. The method further includes forming at least one slit in the valve member, wherein the at least one slit is accessible through the opening and recess.

Another aspect relates to a method of assembling a delivery sheath. The method includes providing an introducer, a valve assembly and an alignment member. The method further includes mounting the valve assembly to a proximal end of the introducer and mounting the alignment member to a proximal end of the valve assembly such that a lumen of the alignment member is aligned with an opening of a valve member within the valve assembly. The lumen of the alignment member is receptive of a medical instrument, the alignment member aligns the medical instrument with the opening of the valve member, and the valve member seals against an outer surface of the medical instrument at at least one location along a length of the medical instrument.

A further aspect relates to a method of assembling a delivery sheath. The method includes providing an introducer, a valve assembly and a flow adapter, positioning the valve assembly at a proximal end of the introducer, and mounting the flow adapter to a proximal end of the valve assembly with a portion of the flow adapter extending through a valve member of the valve assembly. The flow adapter controls fluid flow through the introducer and valve assembly.

The foregoing and other features, utilities, and advantages of the invention will be apparent from the following detailed description of the invention with reference to the accompanying drawings.

BRIEF DESCRIPTION OF THE DRAWINGS

FIG. 12A is a perspective view of the alignment adapter of the sheath assembly shown in FIGS. 1-4.

FIG. 12B is a side view of the alignment adapter shown in FIG. 12A.

FIG. 12C is an end view of the alignment adapter shown in FIG. 12A.

DETAILED DESCRIPTION

Whether active or passive, introducer valves generally suffer from a common disadvantage of failing to provide an effective hemostatic seal with a wide range of sizes of implements and medical devices that are advanced through the valve. Passive valves tend to impose substantial friction forces on many types of implements and medical devices (e.g., large diameter devices), thereby making it difficult for the user to insert and withdraw the implement or medical device relative to the introducer. Moving parts in an active valve have greater potential for failure.

The complexity of common endovascular procedures has placed heightened demands on the ability of the introducer to provide a seal with a variety of implements and medical devices. It is common to have a range in size for such implements and medical devices from various small guidewires (0.01 inch diameter) to relatively large dilators and other implements (e.g., 10 French (F) to 20 F).

The present disclosure is directed to an introducer assembly (also referred to as a delivery sheath) for use in interventional procedures. The introducer assembly may be well suited for use with large bore openings and associated interventional devices. When a large bore introducer is inserted into the arterial system of a patient, it may be important to limit blood from flowing out of a proximal end of the introducer assembly. It may also be important to limit air flow into the introducer assembly and arterial system. The introducer assemblies disclosed herein may include a homeostasis valve designed as a passive valve that limits blood flow out of the proximal end of the introducer assembly, limits air flow into the introducer assembly, and permits various interventional devices to be passed through the valve and into the introducer assembly.

The introducer assembly may include a number of subassemblies that are operable individually or in combination. The subassemblies include an introducer, a valve assembly, an alignment adapter, a flow adapter, and a flush port assembly. The valve assembly may include the passive valve features mentioned above and may be connected at a proximal end of the introducer. The alignment adapter may be mounted at a proximal end of the valve assembly and provide alignment of a medical instrument (e.g., dilator) with a longitudinal axis of the valve assembly when inserting the medical instrument through the valve assembly. Alternatively, a proximal portion of the valve assembly may be extended to eliminate the requirement for the alignment adapter. The flow adapter may be connected to a proximal end of the alignment adapter or may be mounted to the valve assembly. The flow adapter may provide a fluid-to-fluid connection between the internal lumen of the introducer and a proximal end of a device loader. The flush port assembly may provide the option of flushing the introducer assembly with liquid (e.g., saline) to remove air from within the introducer assembly.

Figure 1:
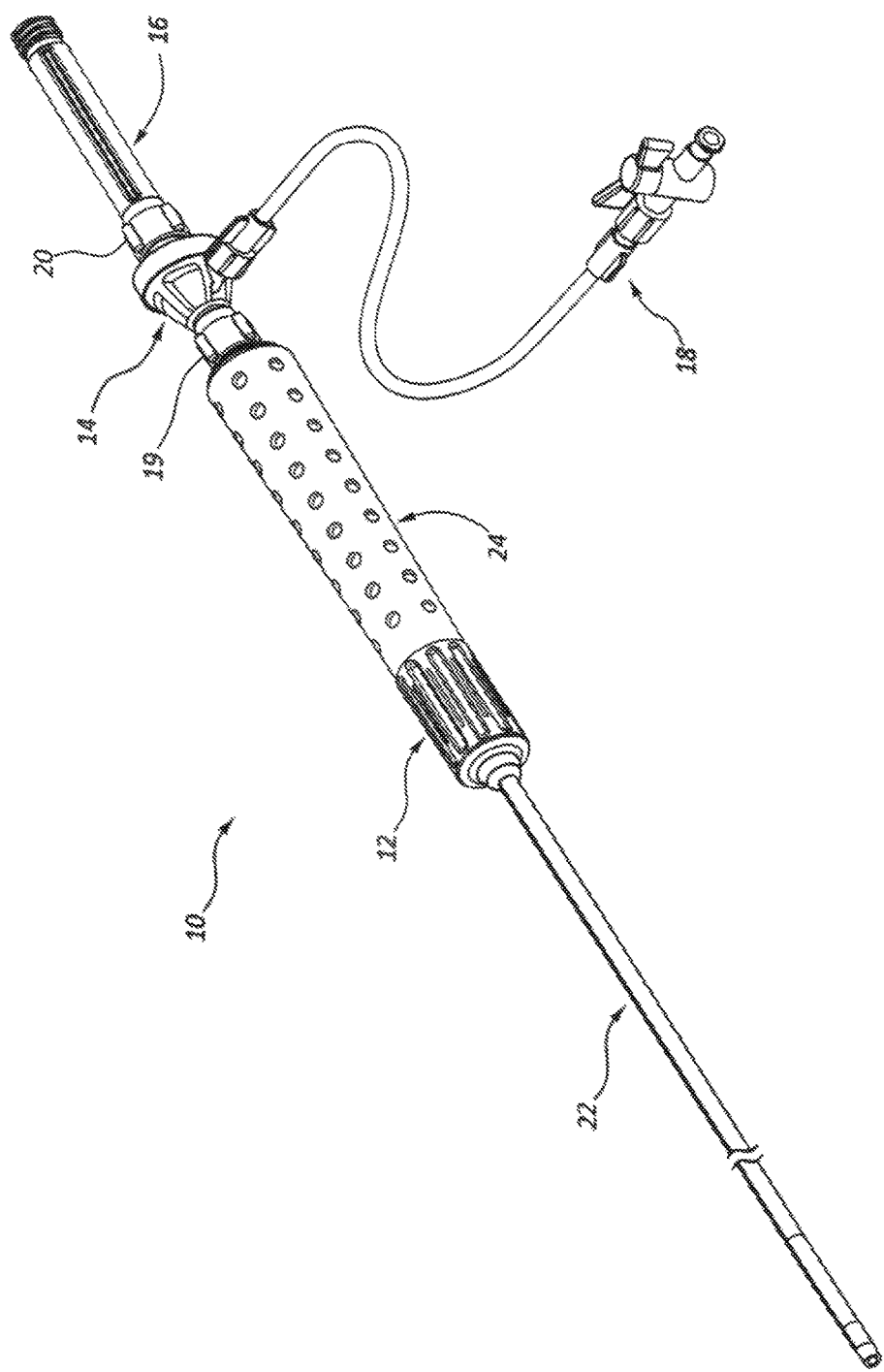
FIG. 1 is a perspective view of a sheath assembly in accordance with the present disclosure.
Figure 2:
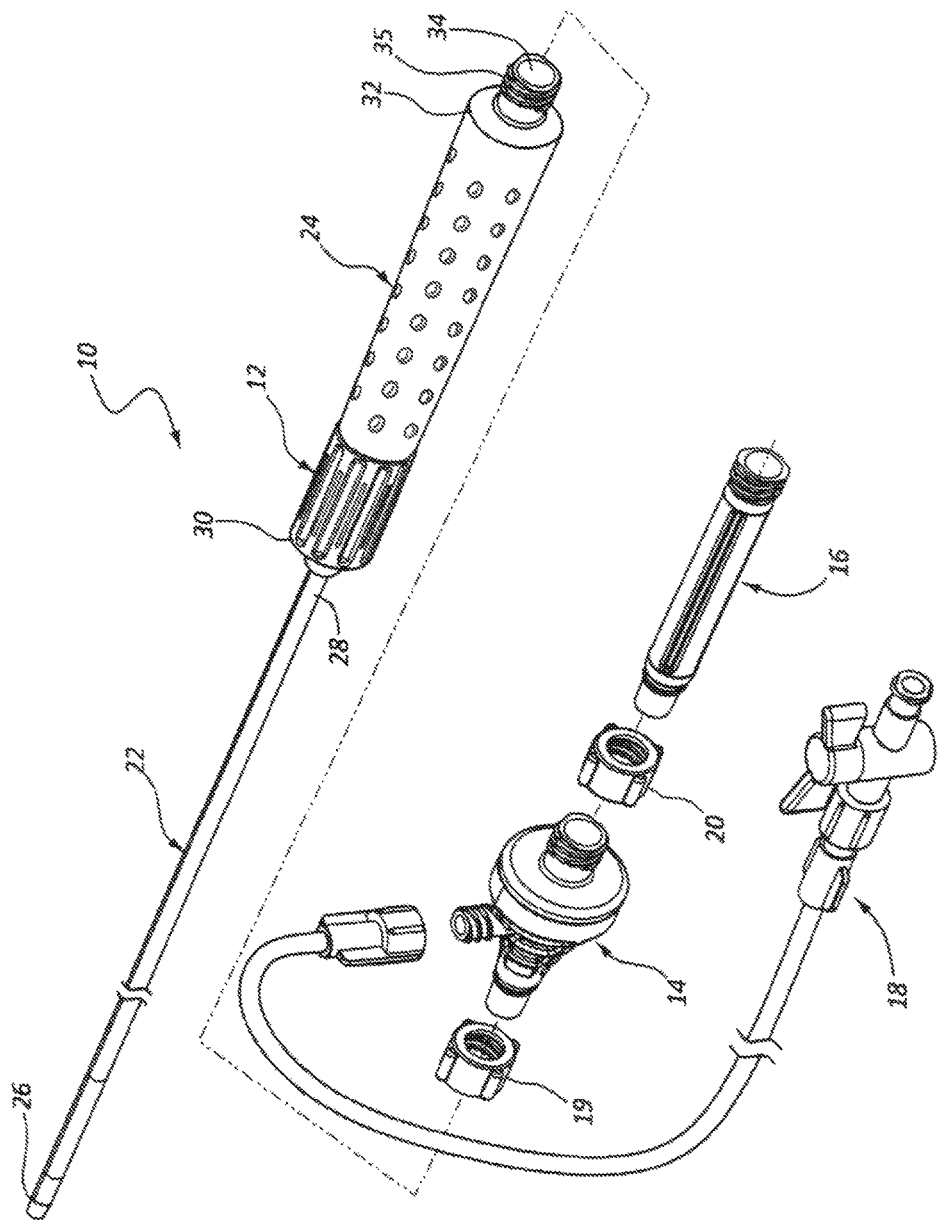
FIG. 2 is an exploded perspective view of the sheath assembly shown in FIG. 1.

Referring now to FIGS. 1-18, and particularly FIGS. 1-2, sheath assembly 10 is shown including introducer 12, valve assembly 14, alignment adapter 16, flush port assembly 18, and first and second connectors 19, 20. Valve assembly 14 is releasably connected to a proximal end of introducer 12 using first connector 19. Alignment adapter 16 is releasably connected to a proximal end of valve assembly 14 using second connector 20. Flush port assembly 18 is coupled in flow communication with valve assembly 14.

Referring to FIG. 2, introducer 12 includes insertion portion 22 and hub 24. Insertion portion 22 includes distal and proximal ends 26, 28. Hub 24 includes distal and proximal ends 30, 32. Lumen 34 may extend through introducer 12 from distal end 26 of insertion portion 22 to proximal end 32 of hub 24. Introducer 12 may be configured as a steerable device, wherein distal end 26 of insertion portion 22 may bend or be steered in at least one direction relative to a longitudinal axis of introducer 12.

Introducer 12 may include connection features 35 at proximal end 32 of hub 24. The connection features may be in the form of, for example, a plurality of threads. Other connection features are possible including, for example, snap-fit or interference-fit connections or fasteners (e.g., screws, rivets or brackets). Connection features 35 may form a mating relationship either directly or indirectly (e.g., via first connector 19) with valve assembly 14 (see FIG. 1). First connector 19 may include a connection feature such as a plurality of threads that mate with connection feature 35 thereby providing releasable attachment of valve assembly 14 to introducer 12. Alternatively, valve assembly 14 may be connected to introducer 12 with a permanent connection using, for example, a bonding agent such as an adhesive.

Lumen 34 may be sized to receive a portion of a medical instrument, which passes through lumen 34 and out of introducer 12 at distal end 26. The medical instrument may include, for example, a guidewire, a dilator, or a closure device.

Second connector 20 may releasably connect alignment adapter 16 to a proximal end of valve assembly 14. Other types of connection features besides the threaded connection provided by second connector 20 may be used to releasably connect alignment adapter 16 to valve assembly 14. Flush port assembly 18 may also be releasably connected to valve assembly 14. For example, a threaded connection may be used to connect flush port assembly 18 to valve assembly 14. Other types of releasably and permanent connection features may be used to couple flush port assembly 18 to valve assembly 14.

Figure 3:
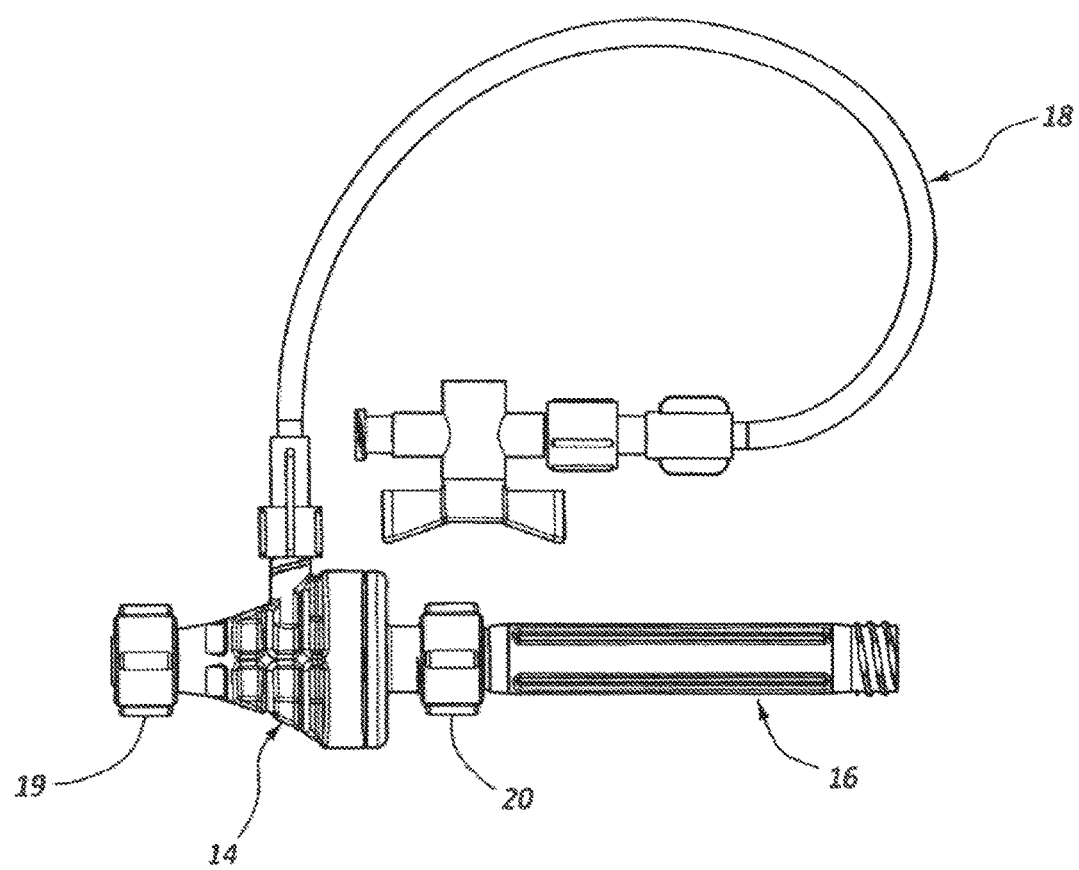
FIG. 3 is a side view of a valve assembly, alignment adapter, and flush port assembly of the sheath assembly shown in FIG. 1.

Referring to FIG. 3, valve assembly 14, alignment adapter 16, and flush port assembly 18 may be used in combination with other types of introducers, sheaths, and other medical devices besides introducer 12. Valve assembly 14, alignment adapter 16, and flush port assembly 18 may be used individually or in other combinations such as, for example, valve assembly 14 and alignment adapter 16 without flush port assembly 18, or valve assembly 14 and flush port assembly 18 without alignment adapter 16. Valve assembly 14, alignment adapter 16, and flush port assembly 18 may be pre-assembled prior to connecting valve assembly 14 to introducer 12. A proximal portion of the valve assembly 14 may be elongated to eliminate the requirement of the separate piece alignment adapter 16.

Figure 4:
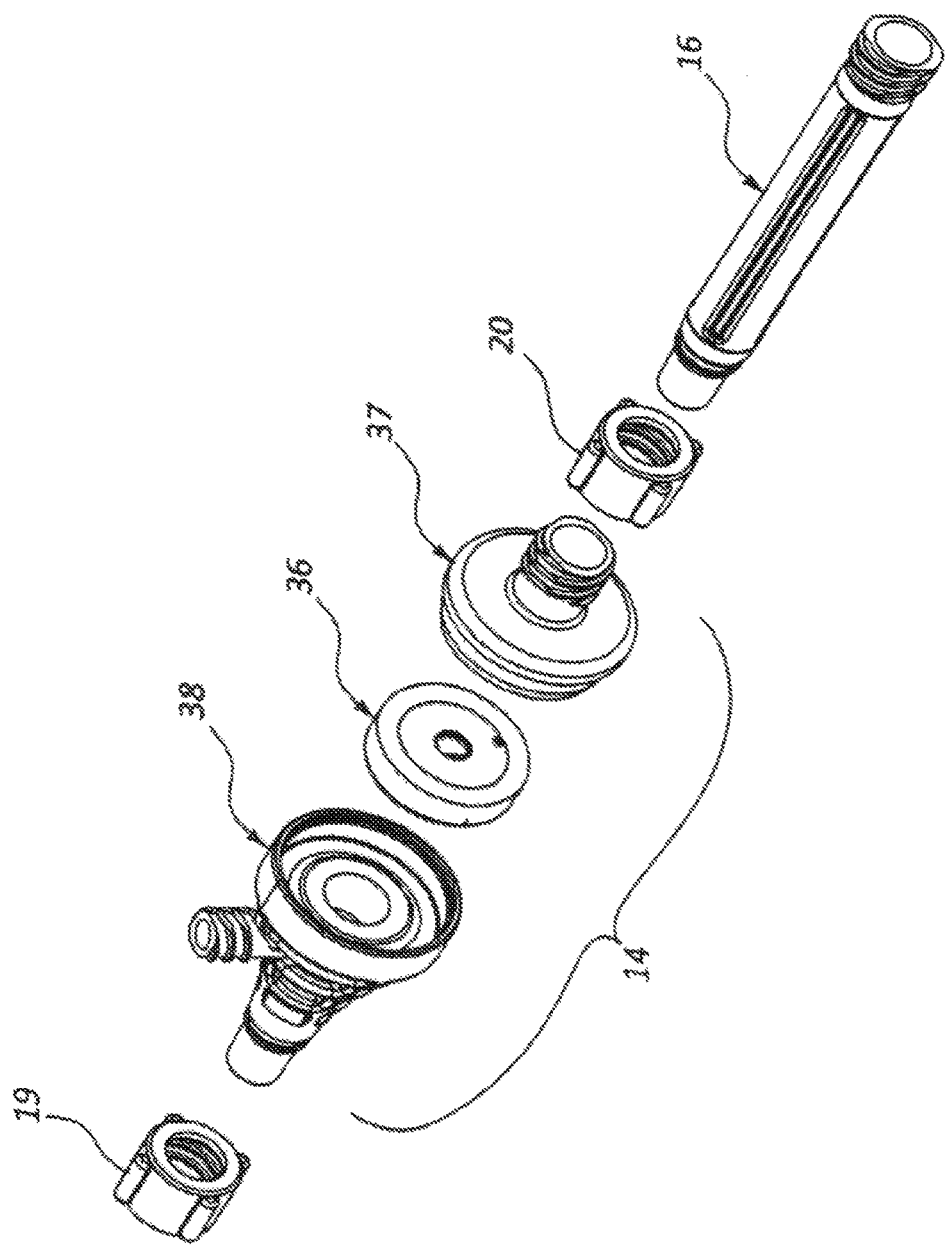
FIG. 4 is an exploded perspective view of the valve assembly and alignment adapter shown in FIG. 3.
Figure 5:
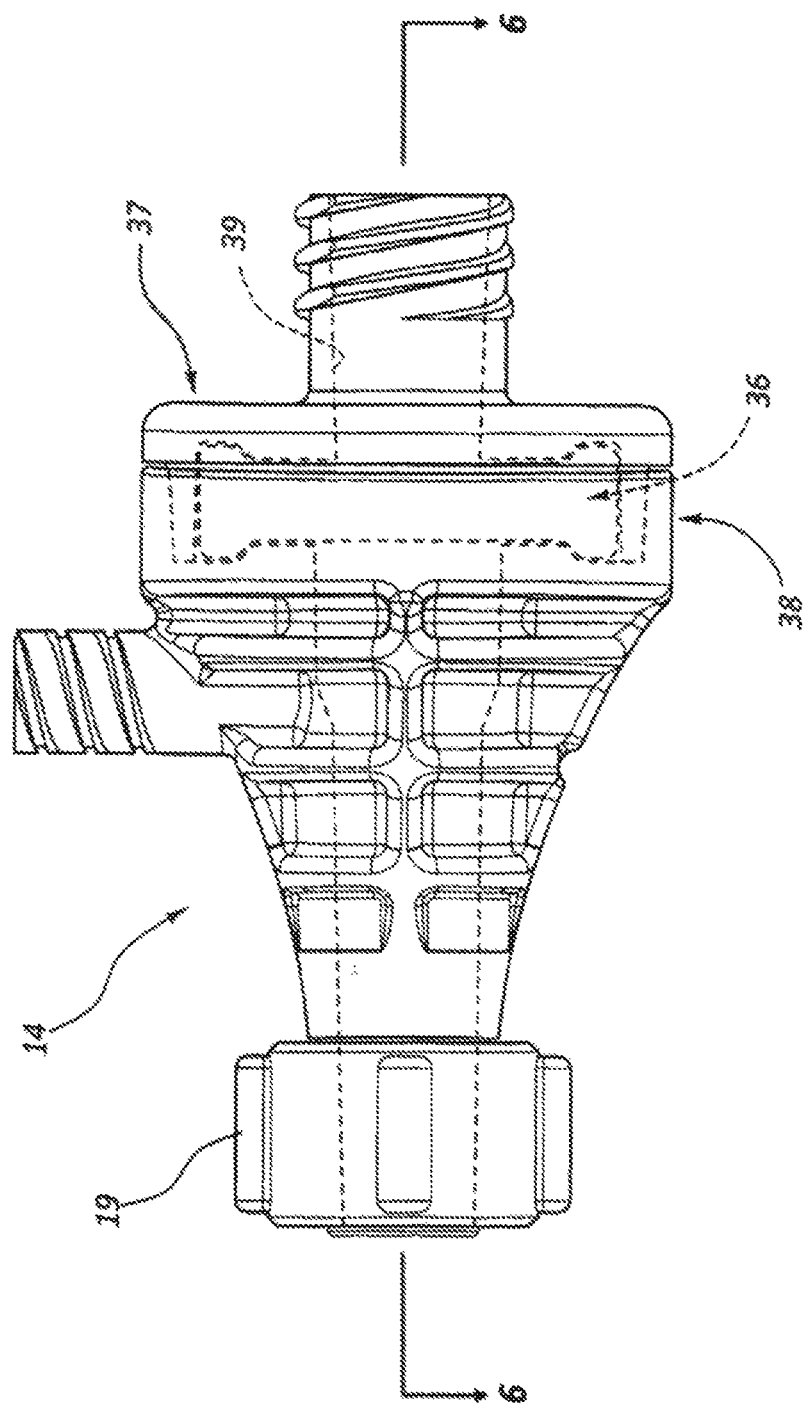
FIG. 5 is a side view of the valve assembly shown in FIG. 3.

Referring now to FIGS. 4 and 5, valve assembly 14 is shown including valve member 36, cap 37, and housing 38. Valve member 36 is captured between cap 37 and housing 38. Cap 37 and housing 38 each define a portion of bore 39 (see FIG. 5) through which a medical instrument is inserted and access to valve 36 is provided. When assembled, valve member 36 provides a sealing interface between cap 37 and housing 38 as shown in the cross-sectional view of FIG. 6. Valve member 36 may provide a fluid-tight seal between cap 37 and housing 38. Valve member 36, cap 37 and housing 38 may be arranged coaxially with each other as further shown in FIG. 6. A medical instrument such as a dilator, guidewire, or other device may inserted through valve assembly 14 as will be described in further detail below related to FIGS. 15-18. Valve member 36 creates a fluid-tight seal between an external surface of the medical instrument and valve assembly 14.

Figure 7B:
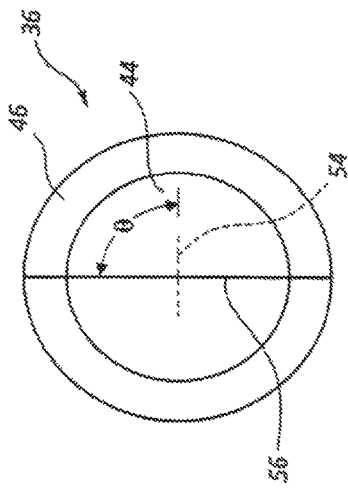
FIG. 7B is a rear review of the valve member shown in FIG. 7A.
Figure 7D:
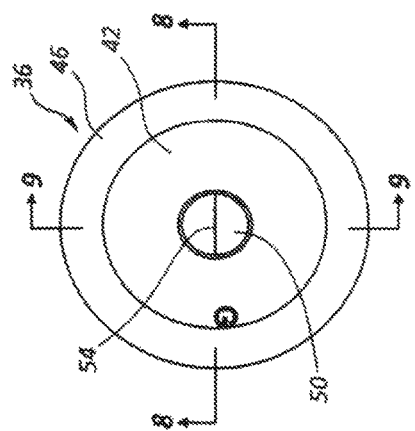
FIG. 7D is a front view of the valve member shown in FIG. 7A.
Figure 7A:
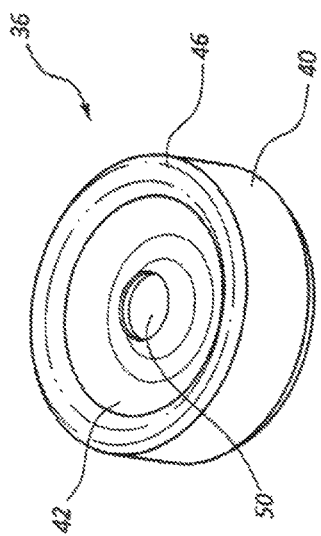
FIG. 7A is a perspective view of a valve member of the valve assembly shown in FIG. 4.
Figure 7C:
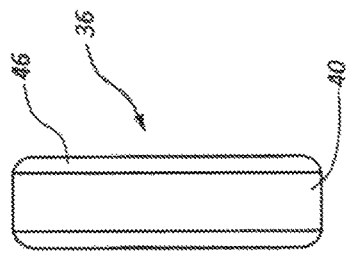
FIG. 7C is a side view of the valve member shown in FIG. 7A.
Figure 8:
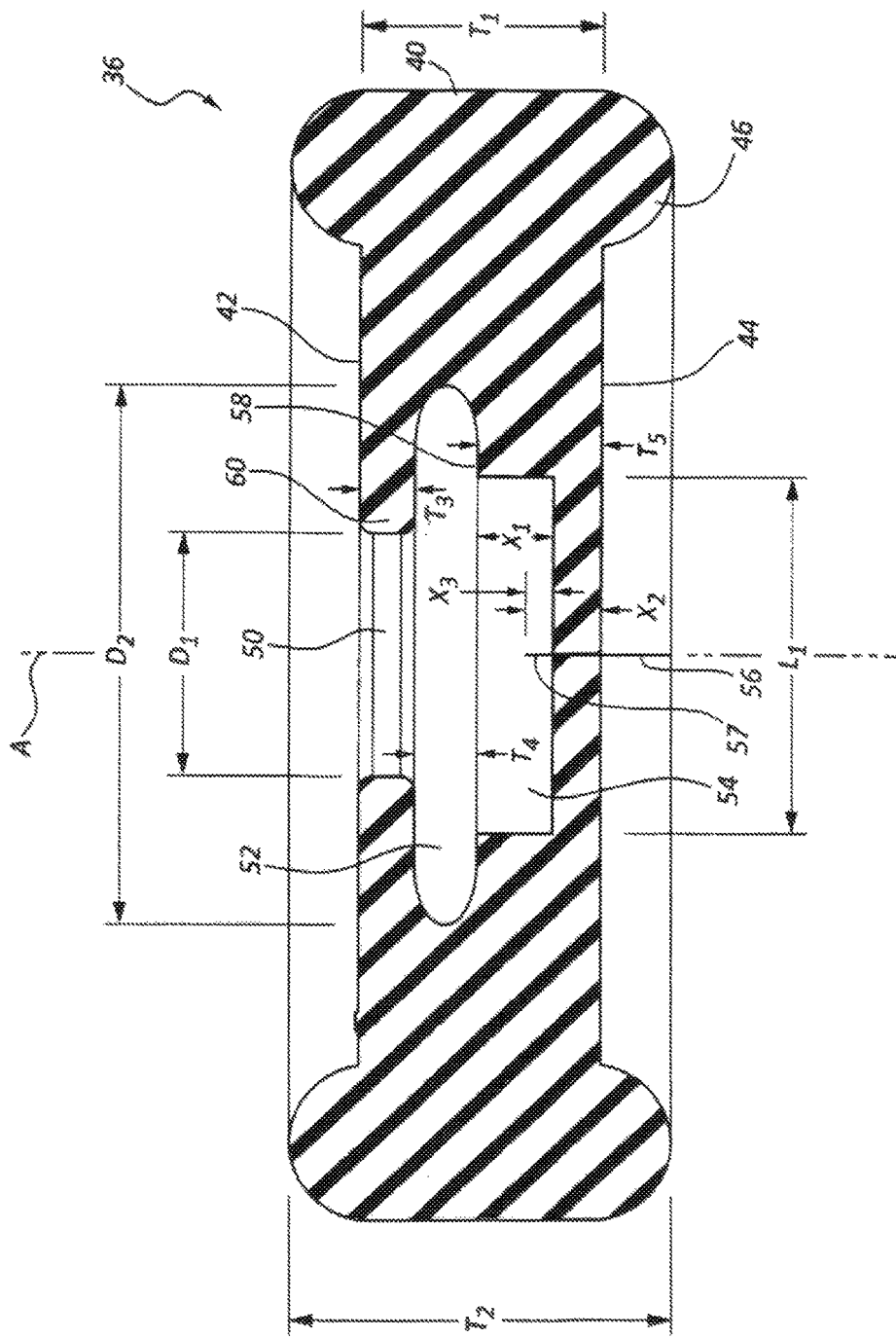
FIG. 8 is a cross-sectional view of the valve member shown in FIG. 7D taken along cross-section indicators 8-8.
Figure 9:
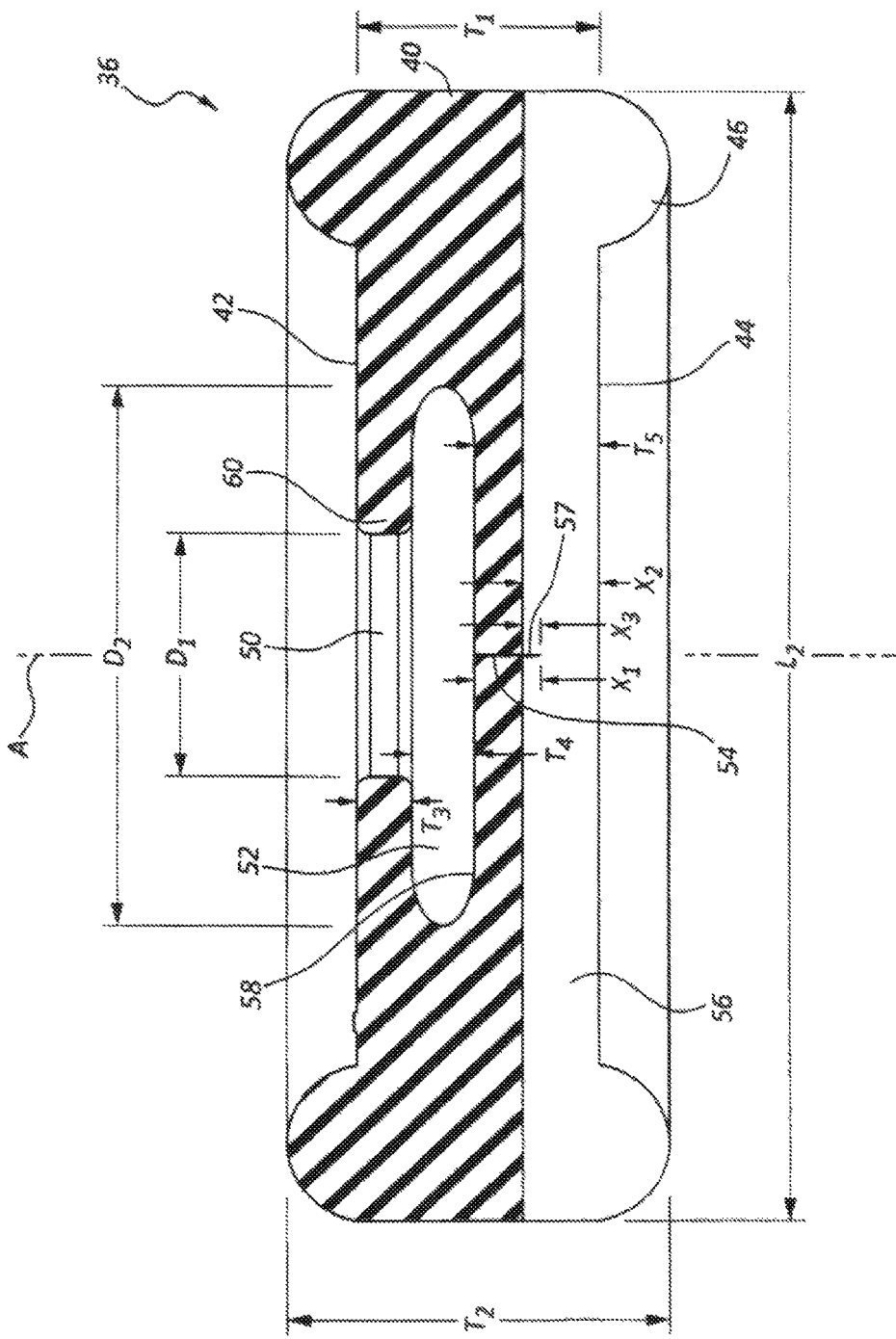
FIG. 9 is a cross-sectional view of the valve member shown in FIG. 7D taken along cross-section indicators 9-9.

Referring now to FIGS. 7A-9, valve member 36 is shown and described in further detail. FIGS. 7A-7D show perspective, rear, side and front views, respectively, of valve member 36. FIGS. 8 and 9 are cross-sectional views taken along cross-section indicators 8-8 and 9-9 of FIG. 7D. FIGS. 8 and 9 also show valve member 36 having perimeter surface 40, first and second primary surfaces 42, 44 arranged opposite of each other, and rim 46 extending around the perimeter surface 40. Valve member 36 also includes opening 50, well 52, and first and second slits 54, 56. First and second slits 54, 56 may include overlapping portion 57. First slit 54 may be formed in and accessible on bottom surface 58 of well 52. Sealing portion 60 may be positioned between opening 50 and well 52.

Rim 46 may extend from at least one of first and second primary surfaces 42, 44. In the depicted embodiment, rim 46 extends axially away from both first and second primary surfaces 42, 44. Rim 46 may help maintain a position of valve member 36 relative to housing 38 and cap 37 when valve assembly 14 is assembled, as shown in FIGS. 1-3.

Valve member 36 may have a thickness $T_1$ measured between first and second primary surfaces 42, 44, as shown in FIG. 8. Rim 46 may have a thickness $T_2$ as shown in FIG. 8. In one example, thickness $T_1$ may be in the range of about 0.1 inch (2.54 mm) to about 0.2 inch (5.08 mm), and more particularly about 0.16 inch (4.06 mm) to about 0.19 inch (4.82 mm). Thickness $T_2$ may be in the range of about 0.2 inch (5.08 mm) to about 0.35 inch (8.89 mm), and more particularly about 0.25 inch (6.35 mm) to about 0.3 inch (7.62 mm). Thickness $T_1$ is typically dependent at least in part on the materials of valve member 36. In one example, valve member 36 comprises silicone material. The silicone material may have a durometor in the range of, for example, about 10 durometor to about 50 durometor, and more particularly about 20 durometor to about 40 durometor. Other materials for use in valve member include, for example, low durometer urethane and low durometer rubber.

Thickness $T_1$ is selected to optimize leak integrity while minimizing the amount of insertion force required to pass a medical instrument through valve member 36. Typically, the smaller the thickness $T_1$ the less leak integrity is provided and the least amount of insertion force is required to pass a medical instrument through valve member 36. The greater the thickness $T_1$ the greater the leak integrity and the greater amount of force is required for insertion of the medical instrument. Further, providing an increased thickness $T_1$ reduces the possibility of tearing or causing other damage to valve member 36 as a result of repeated use or from insertion of relatively large diameter medical instruments.

Opening 50 is formed in first primary surface 42. Opening 50 has a diameter $D_1$. Opening 50 has a thickness $T_2$ measured in a direction from first primary surface 42 toward second primary surface 44. Opening 50 extends coaxially with a central axis A of valve member 36. Opening 50 may have a circular shape. Other shapes are such as an oval shape are possible for opening 50.

The diameter $D_1$ of opening 50 may vary depending on the size of a medical instrument expected to pass through opening 50. Typically, diameter $D_1$ is slightly smaller than the smallest large diameter medical instrument extending through opening 50. The material composition of valve member 36 may permit enlarging of opening 50 as the medical instrument is inserted there through. For example, diameter $D_1$ may increase in size in the range of about 10% to about 100%, and more particularly in the range of about 10% to about 50% in size from a rest state in which no expansion force is applied to opening 50 to an expanded state caused by insertion of the medical instrument.

Well 52 is positioned between opening 50 and first and second slits 54, 56. Well 52 may be positioned in series with opening 50 between first primary surface 42 and second primary surface 44. Well 52 may be referred to as a recess, chamber, or cavity. Well 52 may be formed coaxially with opening 50 and central axis A. Well 52 may have a circular shape. Well 52 may have the same shape as opening 50.

Well 52 has a diameter $D_2$. Diameter $D_2$ is typically greater than $D_1$. Well 52 may extend through thickness $T_4$ between opening 50 and first slit 54. Well 52 may provide a space or cavity within which sealing portion 60 moves as a medical instrument passes through and deforms opening 50. The relatively low durometer, elastic properties of the material of valve member 36 permits some expansion, deformation and/or elastic stretching of sealing portion 60 surrounding opening 50 as sealing portion 60 moves into well 52. The difference in diameter $D_1$ and $D_1$ along with the thickness $T_4$ define at least in part the amount of space available for sealing portion 60 to move into.

Diameter $D_2$ may be relatively constant for a range of diameters $D_1$. For example, diameter $D_2$ may be in the range of about 0.35 inch (8.89 mm) to about 0.5 inch (12.7 mm), and more particularly in the range of about 0.4 inch (10.16 mm) to about 0.43 inch (10.92 mm). Diameter $D_1$ may be in the range of about 0.1 inch (2.54 mm) to about 0.19 inch (4.82 mm) for any given size of $D_2$. Alternatively, the diameter $D_1$ may be proportional to diameter $D_2$ and maintain the proportionality for any given size of opening $D_1$. For example, $D_1$ may be in the range of about 30% to 60% of $D_2$, such as about 50% of $D_2$.

Opening 50 and associated sealing portion 60 may provide a first sealing point between valve member 36 and a medical instrument extending through valve member 36. The seal provided at the first sealing point may be a fluid-tight seal that limits flow of liquids or gases between valve member 36 and the medical instrument passing there through.

First and second slits 54, 56 may be arranged in series between first and second primary surfaces 42, 44. First slit 54 may be formed in bottom surface 58 of well 52 and may extend to a depth $X_1$ and have a length of $L_1$. Second slit 56 may extend from second primary surface 44 towards first slit 54 to a depth $X_2$ and have a length of $L_2$. The depths $X_1$ and $X_2$ may be substantially equal.

First and second slits 54, 56 may have linear shapes along their lengths $L_1$, $L_2$. Other shapes such as contoured shapes along lengths $L_1$, $L_2$ are also possible. Portions of first and second slits 54, 56 may overlap in the axial direction along central axis A to provide overlapping portion 57. Overlapping portion 57 may be oriented at an intersection point between first and second slits 54, 56 and may also be referred to as intersection point 57 or intersection 57. Overlapping portion 57 has a depth $X_3$ that is usually less than $X_1$ and $X_2$.

First and second slits 54, 56 may provide a pathway or a channel that extends from bottom surface 58 to second primary surface 44. The portion of valve member 36 through which first and second slits 54, 56 extend may have a thickness $T_5$. The thickness $T_5$ may be in the range of, for example, about 0.08 inch (2.03 mm) to about 0.1 inch (2.54 mm), and more particularly in the range of about 0.85 inch (21.6 mm) to about 0.95 inch (24.13 mm).

The depths $X_1$ and $X_2$ may be in the range of, for example, about 0.3 inch (7.62 mm) to about 0.6 inch (15.24 mm), and more particularly in the range of about 0.4 inch (10.16 mm) to about 0.5 inch (12.7 mm). Depth $X_1$ of overlapping portion 57 may be in the range of, for example, about 0.01 inch (0.254 mm) to about 0.1 inch (2.54 mm), and more particularly in the range of about 0.015 inch (0.381 mm) to about 0.03 inch (0.762 mm).

The lengths $L_1$, $L_2$ may vary depending on the various conditions and features of valve member 36. For example, $L_1$ may be limited by the diameter $D_2$ of well 52. Typically, diameter $D_1$ of first slit 54 is less than diameter $D_2$. First slit 54 may be formed by inserting an instrument such as cutting device through opening 50 and well 52 and into contact with bottom surface 58.

Second slit 56 is formed in second primary surface 44. Length $L_2$ of second slit 56 may have fewer constraints. Length $L_2$ may be as great as a maximum diameter of valve member 36, as shown in the figures. In other arrangements, length $L_2$ is equal to or less than the length $L_1$. In one example, length $L_1$ is in the range of about 0.25 inch (6.35 mm) to about 0.3 inch (7.62 mm), and more preferably about 0.27 inch (6.86 mm) to about 0.28 inch (7.11 mm). Length $L_2$ may be in the range of, for example, about 0.8 inch (20.32 mm) to about 0.95 inch (24.13 mm), and more particularly in the range of about 0.85 inch (21.59 mm) to about 0.89 inch (22.61 mm).

First and second slits 54, 56 may be arranged at an angle θ relative to each other as shown in FIG. 7B. The angle θ may be in the range of about, for example, about 45° to about 90°. First and second slits 54, 56 may be arranged generally perpendicularly to each other and may be referred to as intersecting slits. While two slits 54, 56 are shown, other slit arrangements are possible including a single slit, or three or more slits.

Figure 10:
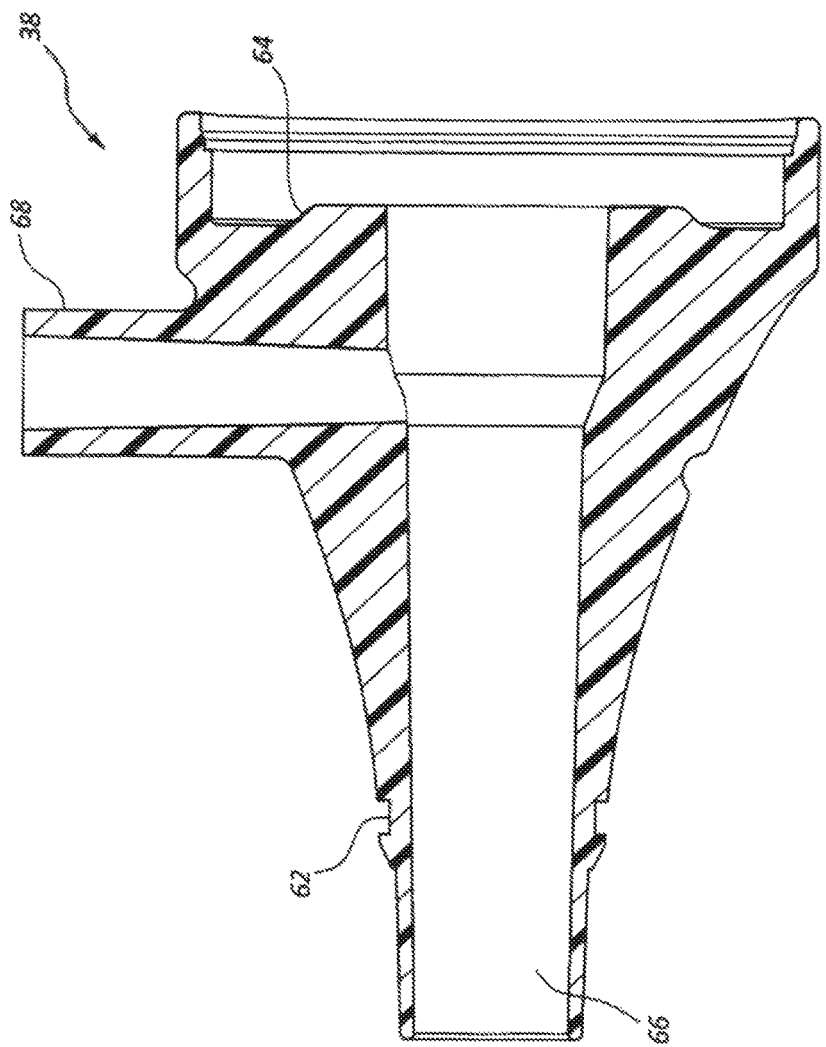
FIG. 10 is a cross-sectional view of a housing member of the valve assembly shown in FIG. 4

Referring now to FIG. 10, housing 38 is shown including distal connection portion 62, first valve seat 64, central bore 66, and flush port 68. Distal connection portion 62 may be connected to first connector 19 and used to secure valve assembly 14 to introducer 12. First valve seat 64 may include a recess and be sized and arranged to receive a portion of rim 46 of valve member 36 (e.g., see FIG. 6). Central bore 66 may be aligned coaxially with opening 50, well 52, and intersection 57 of first and second slits 54, 56 along the central axis A of valve member 36. Flush port 68 may be coupled in fluid communication with flush port assembly 18. Flush port assembly 18 may be releaseably connected to housing 38 at flush port 68. Flush port 68 may intersect central bore 66 at a location distal of first valve seat 64 and valve member 36.

Figure 6:
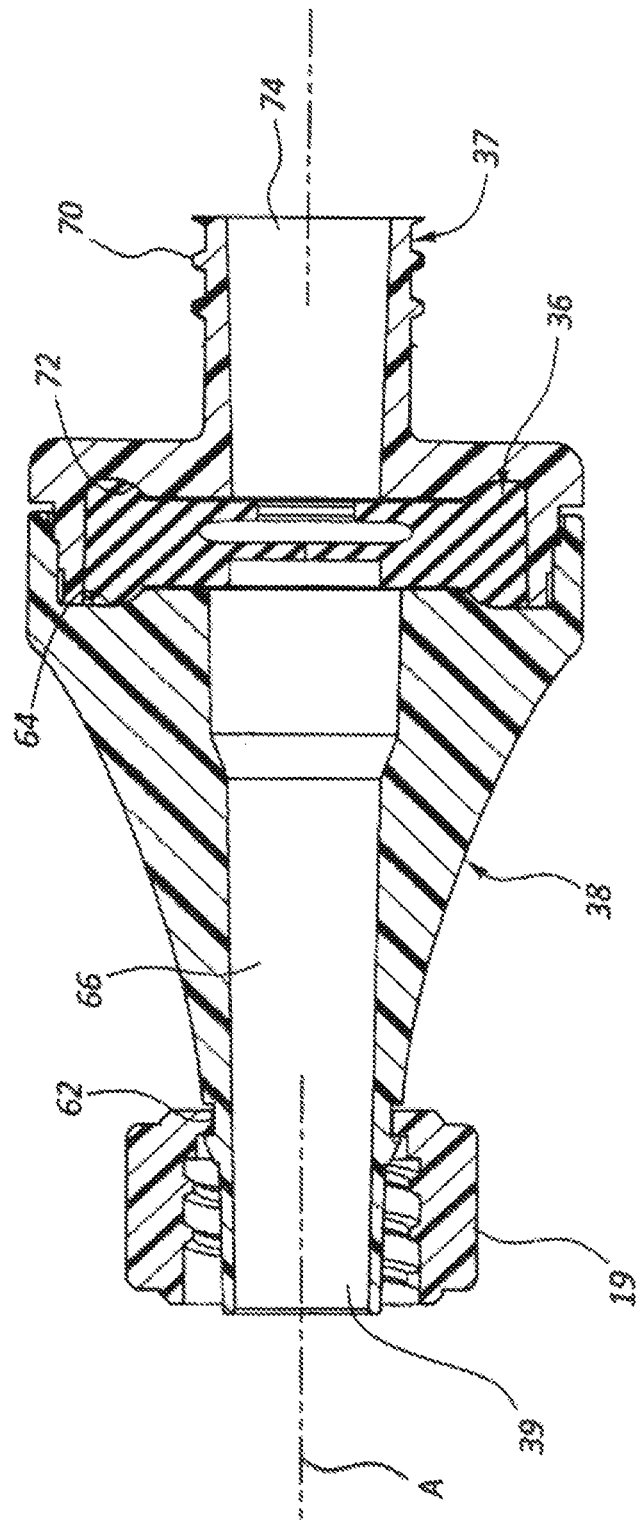
FIG. 6 is a cross-sectional view of the valve assembly shown in FIG. 5 taken along cross-section indicators 6-6.
Figure 11:
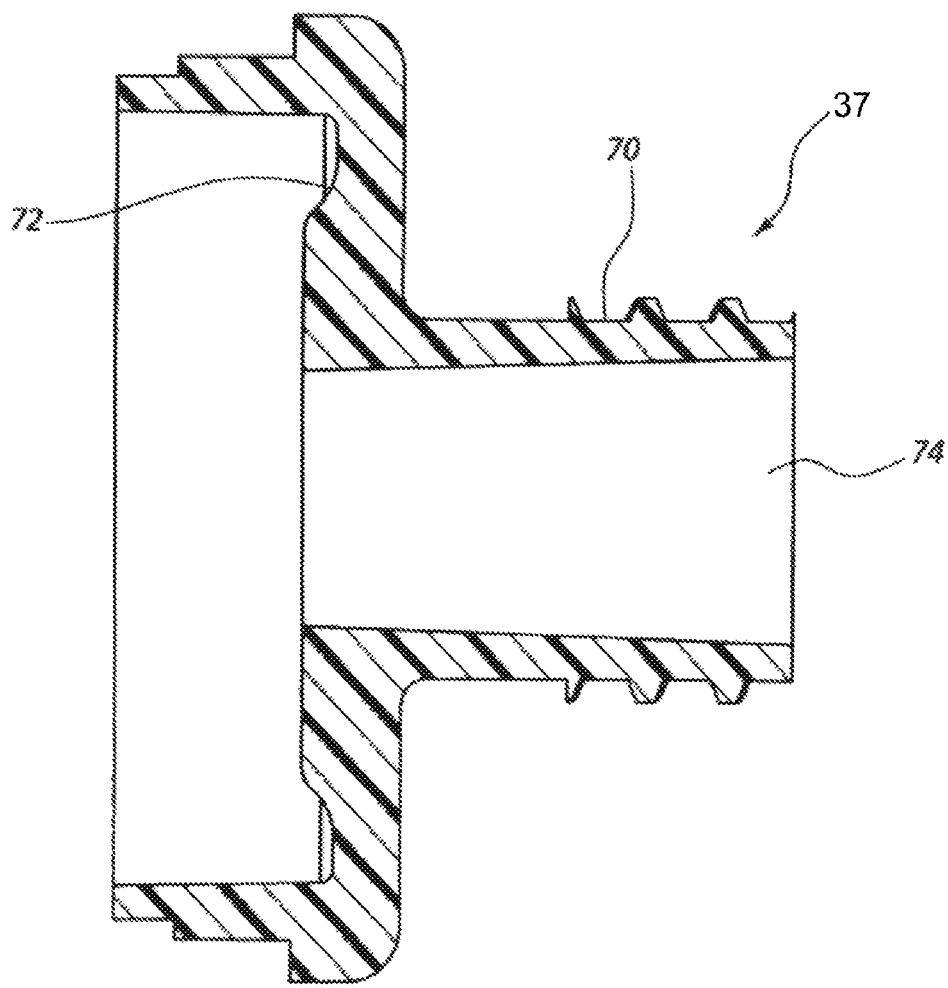
FIG. 11 is a cross-sectional view of a cap of the valve assembly shown in FIG. 6.
Figure 13:
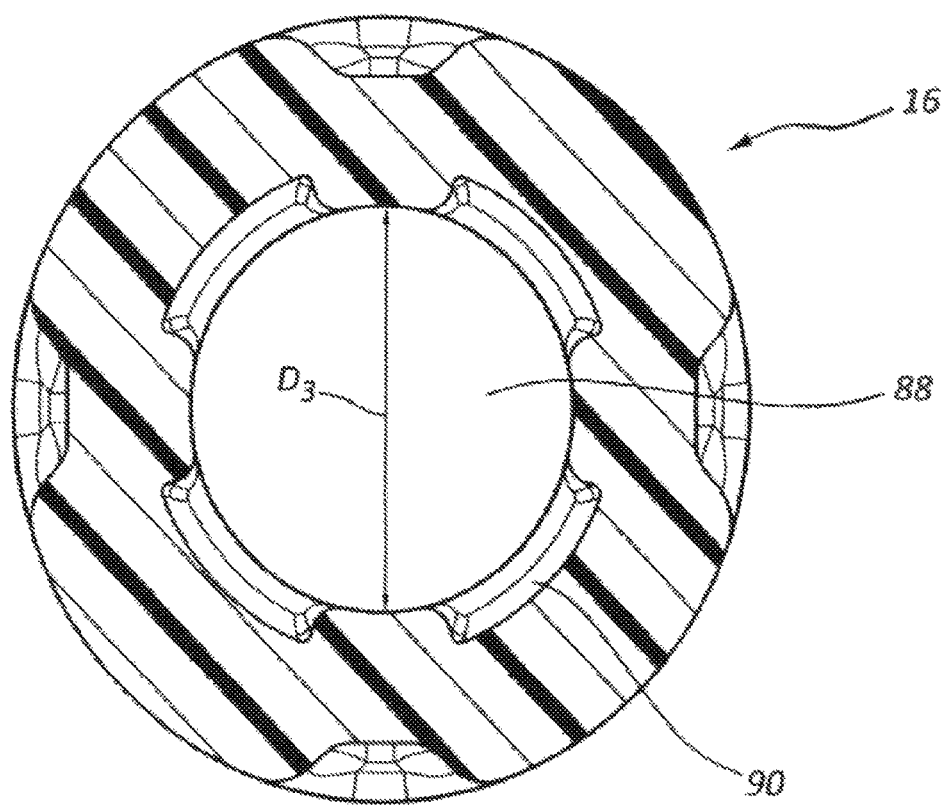
FIG. 13 is a cross-sectional view of the alignment adapter shown in FIG. 12B taken along cross-section indicators 13-13.
Figure 14:
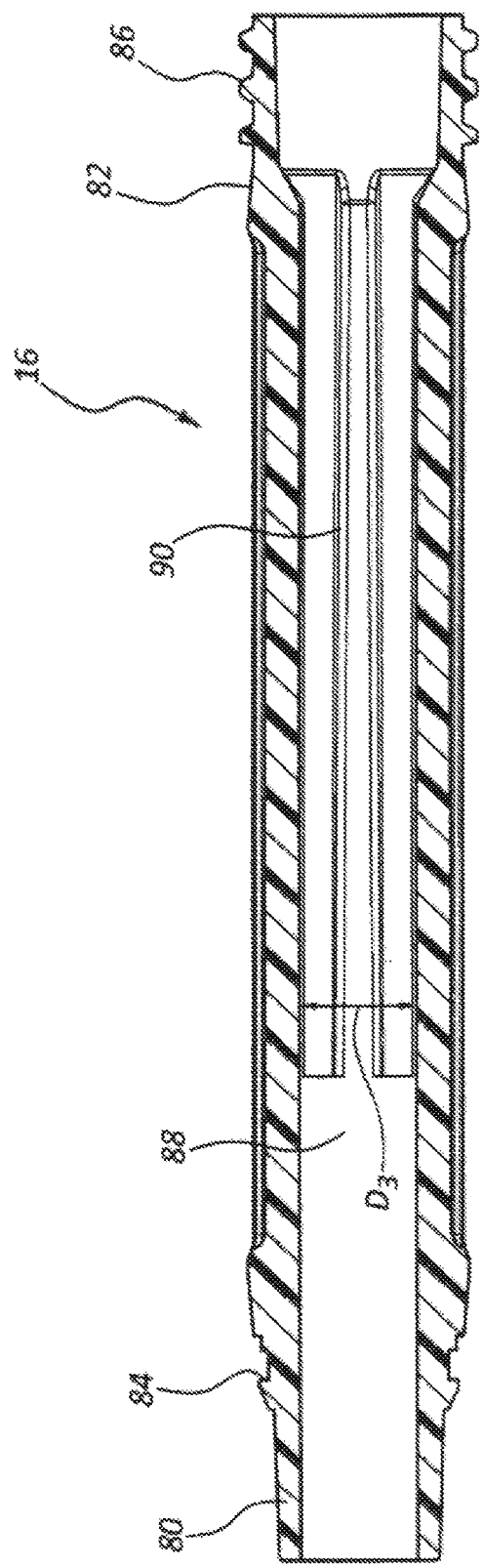
FIG. 14 is a cross-sectional view of the alignment adapter shown in FIG. 12B taken along cross-section indicators 14-14.

FIG. 11 shows cap 37 having proximal connection portion 70, second valve seat 72, and central bore 74. Proximal connection portion 70 may include connection features such as a plurality of threads to permit releasable connection of valve assembly 14 to alignment adapter 16 via second connector 20. Second valve seat 72 may include a recess or other feature which interfaces with valve member 36 (e.g., rim 46 as shown in FIG. 6). Securing cap 37 to housing 38 may capture valve member 36 there between. Housing 38 and cap 37, when connected together, may provide an axial compression force to valve member 36 (e.g., to rim 46) which holds valve member 36 in fixed axial and rotational positions. Central bore 74 may be aligned coaxially with opening 50, well 52, and intersection 57 of first and second slits 54, 56 along central axis A of valve member 36. Opening 50 may be open to and face central bore 74 of cap 37.

Cap 37 may be releaseably connected to housing 38. A releasable connection may permit access to valve member 36 to replace or repair valve member 36. Alternatively, cap 37 may be permanently connected to housing 38. Cap 37 may be connected to housing 38 using various connection features including, for example, snap-fit and interference-fit connections, a bonding agent or fasteners. Other connection methods include, for example, heat welding, laser welding, or sonic welding.

When using a low durometor material for valve member 36, it may be advantageous to accurately align the medical instrument centrally with opening 50 and intersection 57 of first and second slits 54, 56 prior to and during insertion of the medical instrument through valve member 36. Such alignment may help avoid damage to valve member 36 which might otherwise occur if the medical instrument contacts valve member 36 at off center locations. Typically, central bore 74 of cap 37 has a greater minimum internal diameter than the maximum diameter of the medical instrument inserted there through and into contact with valve member 36. It may be difficult for the operator to accurately align the medical instrument along central axis A without assistance from an alignment device. Alignment adapter 16 may provide such alignment of the medical instrument.

Alignment adapter 16 is shown in FIGS. 12A-14. FIGS. 12A and 12B show alignment adapter 16 having distal and proximal ends 80, 82, distal connection feature 84, and proximal end connection feature 86. Distal connection feature 84 may cooperate with second connector 20 to releasably connect alignment adapter 16 to valve assembly 14 (see FIG. 3). Distal end 80 may be inserted into central bore 74 of cap 37. Second connector 20 may be mounted to alignment adapter 16 at distal connection feature 84 and provide releasable connection with proximal connection portion 70 of cap 37. Proximal connection feature 86 may include, for example, a plurality of threads to provide a releasable connection with connection features of a medical device.

Referring to FIGS. 12C-14, alignment adapter 16 may further include insertion lumen 88 and a plurality of internal alignment members 90 positioned in insertion lumen 88. Internal alignment members 90 may extend radially inward into insertion lumen 88. Internal alignment members 90 may define an opening size (e.g., diameter $D_3$) for insertion of a medical instrument through alignment adapter 16. The diameter $D_3$ defines a maximum external dimension (e.g., diameter) of the medical instrument inserted through alignment adapter 16 and into valve assembly 14. Diameter $D_3$ may be at least as great as diameter $D_1$ of opening 50.

Internal alignment members 90 may be adjusted to create different sizes for diameter $D_3$, which sizes may be customized for specific sized medical instruments. Alignment members 90 may be circumferentially spaced apart around an inner surface of alignment adapter 16. Other portions of alignment adapter 16 may remain constant in size and shape for use with a plurality of different diameters $D_3$ defined by internal alignment members 90. For example, one alignment adapter 16 may have internal alignment members 90 that define a diameter $D_3$ sized to accommodate a 12 F or smaller medical instrument. The diameter $D_3$ may be slightly larger than 12 F. Another alignment adapter 16 may have different sized internal alignment members 90 which create a diameter $D_3$ sized to accommodate 17 F or smaller medical instruments, wherein the diameter $D_3$ is slightly larger than 17 F.

Typically, the closer in size $D_3$ is to an outer dimension of the medical instrument inserted there through (e.g., a dilator), the better alignment adapter 16 is able .to accurately align the inserted medical instrument with intersection 57 of first and second slits 54, 56 and central axis A of valve member 36.

Alignment adapter 16 may have particular relevance when inserting a dilator through valve assembly 14. Typically, a dilator has a relatively large diameter and is used to expand and/or stretch a puncture or opening at a treatment site within the patient prior to delivering a treatment device to the treatment site. The dilator is removed prior to inserting the treatment device through introducer 12 and valve assembly 14. In at least some arrangements, alignment adapter 16 is removed from valve assembly 14 prior to inserting the treatment device or other medical instrument. In other arrangements, alignment adapter 16 remains connected to valve assembly 14 after removal of the dilator and during insertion of another medical instrument through sheath assembly 10.

In some arrangements, alignment adapter 16 is integrated into valve assembly 14. For example, cap 37 may have an elongate proximal portion having at least some of the features of alignment adapter 16 (e.g., insertion lumen 88 and internal alignment members 90). A separate cap 37, which is customized for use with a particular sized medical instrument, may be used for each application of valve assembly 14. Typically, alignment adapter 16, whether formed independently or integrally with valve assembly 14, has a length $L_3$ (see FIG. 12B) which is at least as long as a tapered distal end of the medical instrument (e.g., dilator) being inserted through alignment adapter 16. Length $L_3$ may be in the range of, for example, about 1 inch (25.4 mm) to about 5 inch (127 mm), and more particularly in the range of about 2 inch mm) to about 3 inch (76.2 mm) Length $L_3$ is typically selected to accommodate a wide range of medical instrument diameters and the length of their associated tapered distal tips.

Figure 15:
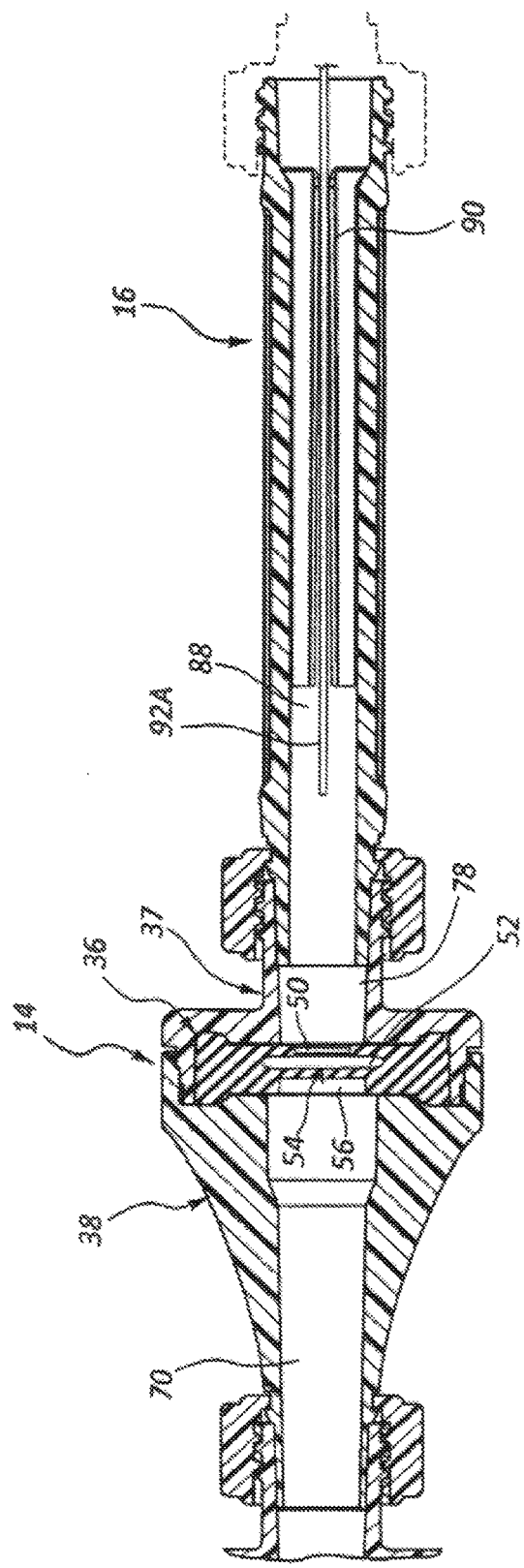
FIG. 15 is a cross-sectional view of the valve assembly and alignment adapter shown in FIG. 1 with a guidewire partially inserted therein.
Figure 16:
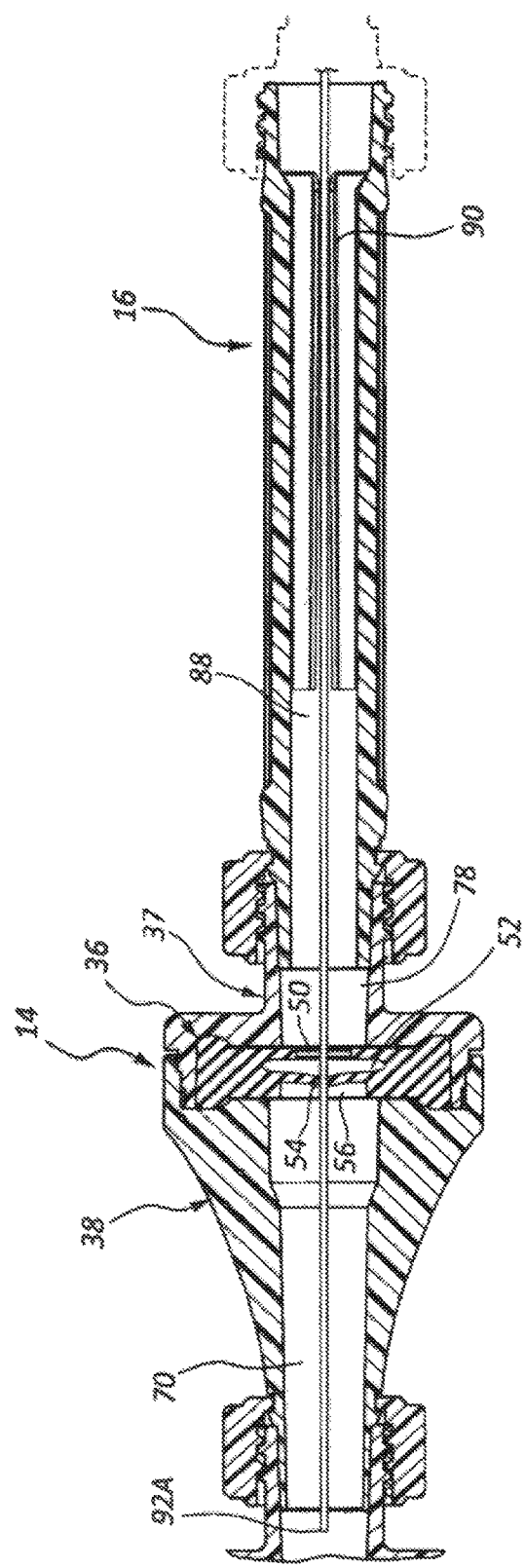
FIG. 16 shows the valve assembly and alignment adapter shown in FIG. 15 with the guidewire inserted through the valve member.

FIGS. 15-18 show use of sheath assembly 10 to deliver medical instruments across valve member 36. FIGS. 15 and 16 show medical instrument 92A in the form of a guidewire. The guidewire may have an outer diameter in the range of, for example, about 0.02 inch (0.51 mm) to about 0.05 inch (1.27 mm), and more particularly about 0.03 inch (0.762 mm). Typically, the diameter of medical instrument 92A is less than the diameter $D_1$ of opening 50. FIG. 15 shows medical instrument 92A located within alignment adapter 16 but spaced proximal of valve member 36. FIG. 16 shows medical instrument 92A inserted through valve member 36. Valve member 36 provides a sealed connection along an exterior surface of medical instrument 92A in the area of first and second slits 54, 56. The smaller diameter of medical instrument 92A, which is less than the diameter of opening 50, may eliminate contact between sealing portion 60 and medical instrument 92A.

The small diameter size of medical instrument 92A may limit the influence of alignment adapter 16 on aligning medical instrument 92A with intersection 57 of first and second slits 54, 56. In other embodiments, alignment adapter 16 may have an internal diameter that is sized closer to the diameter of medical instrument 92A to provide the intended alignment with intersection 57 of first and second slits 54, 56.

Figure 17:
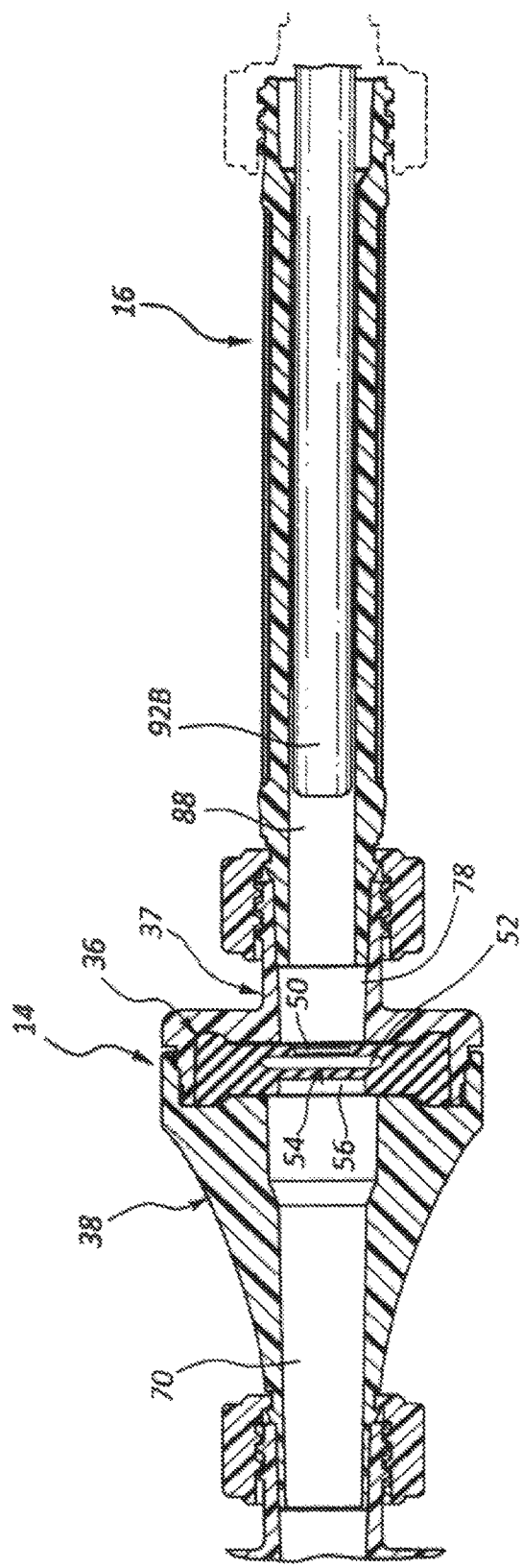
FIG. 17 is a cross-sectional view of the valve assembly alignment and adapter shown in FIG. 1 with a dilator partially inserted therein.
Figure 18:
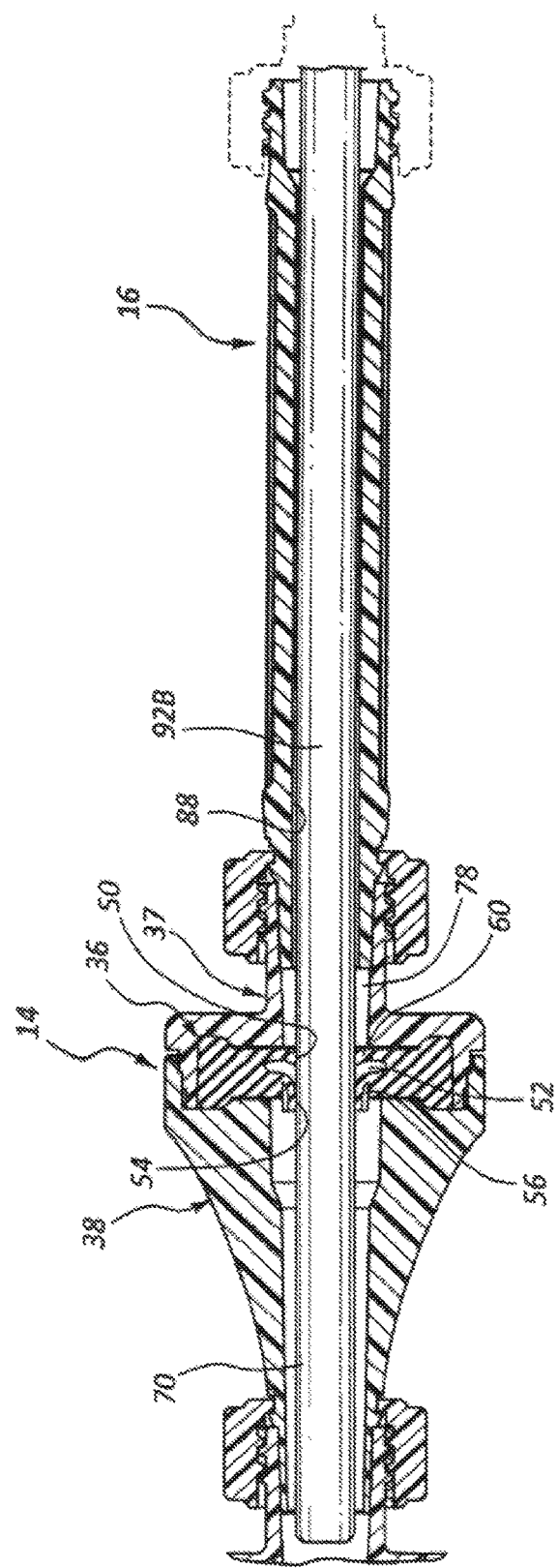
FIG. 18 shows the valve assembly and alignment adapter shown in FIG. 17 with the dilator inserted through the valve member.

FIGS. 17 and 18 show insertion of medical instrument 92B through sheath assembly 10. Medical instrument 92B has a greater diameter than the diameter of medical instrument 92A. The diameter of medical instrument 92B may be greater than the diameter of opening 50. FIG. 17 shows medical instrument 92B located within alignment adapter 16, but spaced proximal of valve member 36. FIG. 18 shows medical instrument 92B extending through valve member 36.

Valve member 36 provides two sealing points along the length of medical instrument 92B. A first sealing point is provided between sealing portion 60 and an external surface of medical instrument 92B in the area of opening 50 and well 52, as shown in FIG. 18. Sealing portion 60 deforms both radially outward and axially in a distal direction as medical instrument 92B is inserted through opening 50. A second sealing point is provided between valve member 36 and medical instrument 92B in the area of first and second slits 54, 56, as shown in FIG. 18. The material of valve member 36 between bottom surface 58 of well 52 and second primary surface 44 (e.g., see FIG. 8) deforms in a radially outward direction and in an axial direction distally as medical instrument 92B is inserted through first and second slits 54, 56, as shown in FIG. 18. Valve member 36 provides first and second axially spaced apart sealing interfaces with medical instrument 92B. Valve member 36 provides at least one fluid-tight interface with medical instrument 92B which limits backflow of fluids in a proximal direction and inflow of air in a distal direction through valve member 36.

After medical instrument 92B is removed from sheath assembly 10, valve member 36 may elastically return to its initial or rest position shown in FIG. 17. Valve member 36 may provide a fluid-tight seal through first and second slits 54, 56 after removal of medical instrument 92B. The elastic, resilient properties of valve member 36 pay permit multiple, repeated insertions of a given medical instrument or insertion of a plurality of different medical instruments while maintaining leak integrity. A single configuration for valve member 36 (e.g., a valve member having a given opening size and slit configuration) may be operable to provide at least one sealed interface with medical instruments of various sizes (e.g., outer diameter). Valve member 36 may provide multiple sealed interfaces with at least some sizes of medical instruments inserted there through if the maximum outer dimension of the medical instrument is at least as great as the diameter of opening 50.

Referring again to FIGS. 1-5, flush port assembly 18 may be releaseably mounted to flush port 68 (shown in FIG. 10) of housing 38. Flush port assembly 18 may provide control of fluid flow at a location distal of valve member 36. For example, flush port assembly 18 may be coupled to a vacuum source to remove fluids (e.g., blood or air) from within sheath assembly 10 at a location distal of valve member 36. Alternatively, flush port assembly 18 may be coupled to a source of liquid such as saline to flush fluids from sheath assembly 10.

Figure 19:
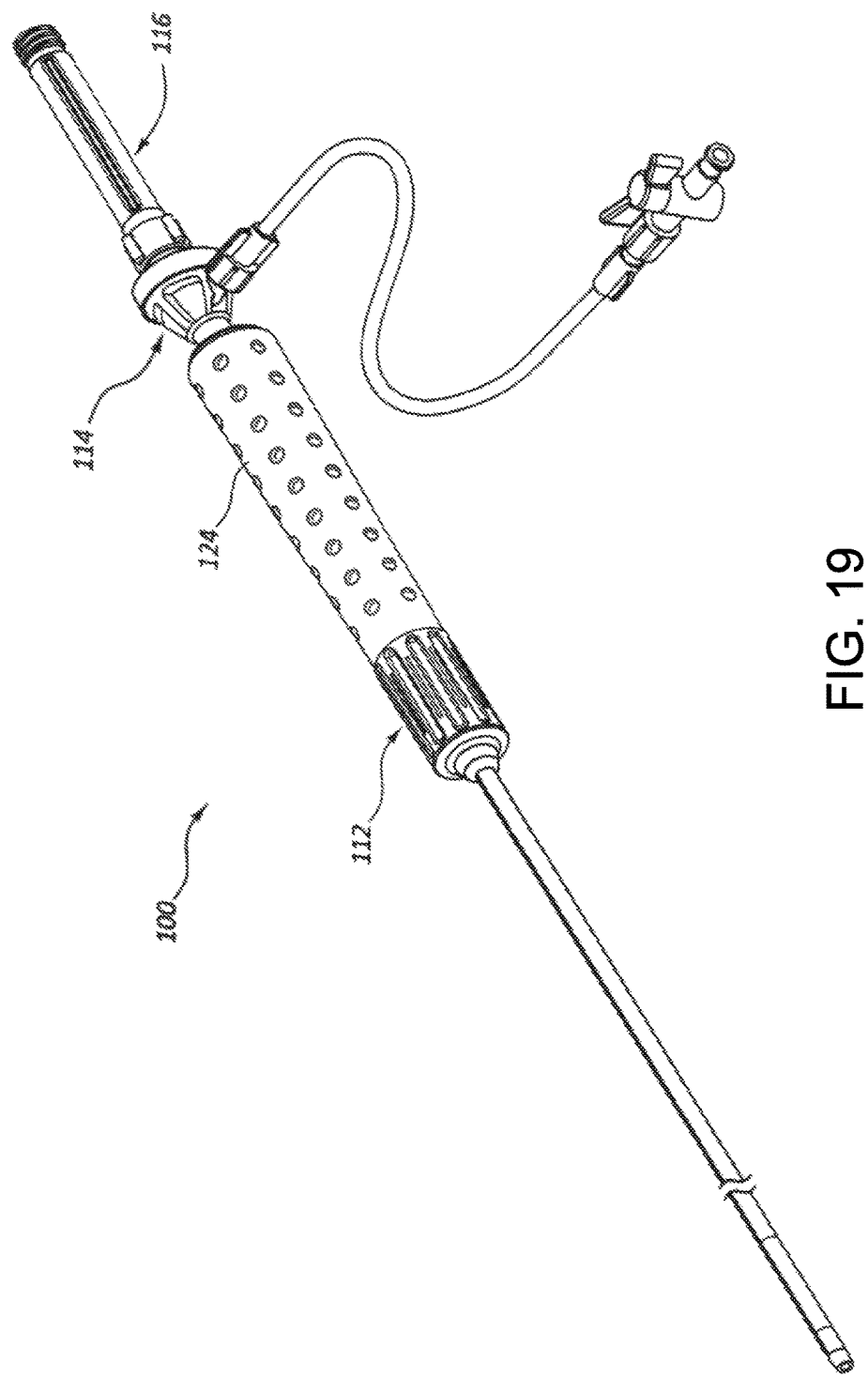
FIG. 19 is a perspective view of a sheath assembly with an integrated valve assembly in accordance with the present disclosure.

As mentioned above, various features of sheath assembly 10 may be provided as individual, separate parts, which may be releaseably connected to each other, or may be formed integrally with each other. FIG. 19 shows another sheath assembly 100 having introducer 112, valve assembly 114, and alignment adapter 116. Valve assembly 114 is integrally formed with introducer 112. Valve assembly 114 may be permanently connected to introducer 112. In one example, valve assembly 114 is co-molded with features of introducer 112. Alternatively, valve assembly 114 may be bonded using an adhesive or be solvent bonded. A separate connector (e.g., first connector 19) may be eliminated from sheath assembly 100. At least portions of valve assembly 114 may be integrated into hub 124 of introducer 112 and may be positioned internal to hub 124.

Portions of alignment adapter 116 may be permanently connected to valve assembly 114. Portions of alignment adapter 116 may be integrated into a portion of valve assembly 114.

Figure 20:
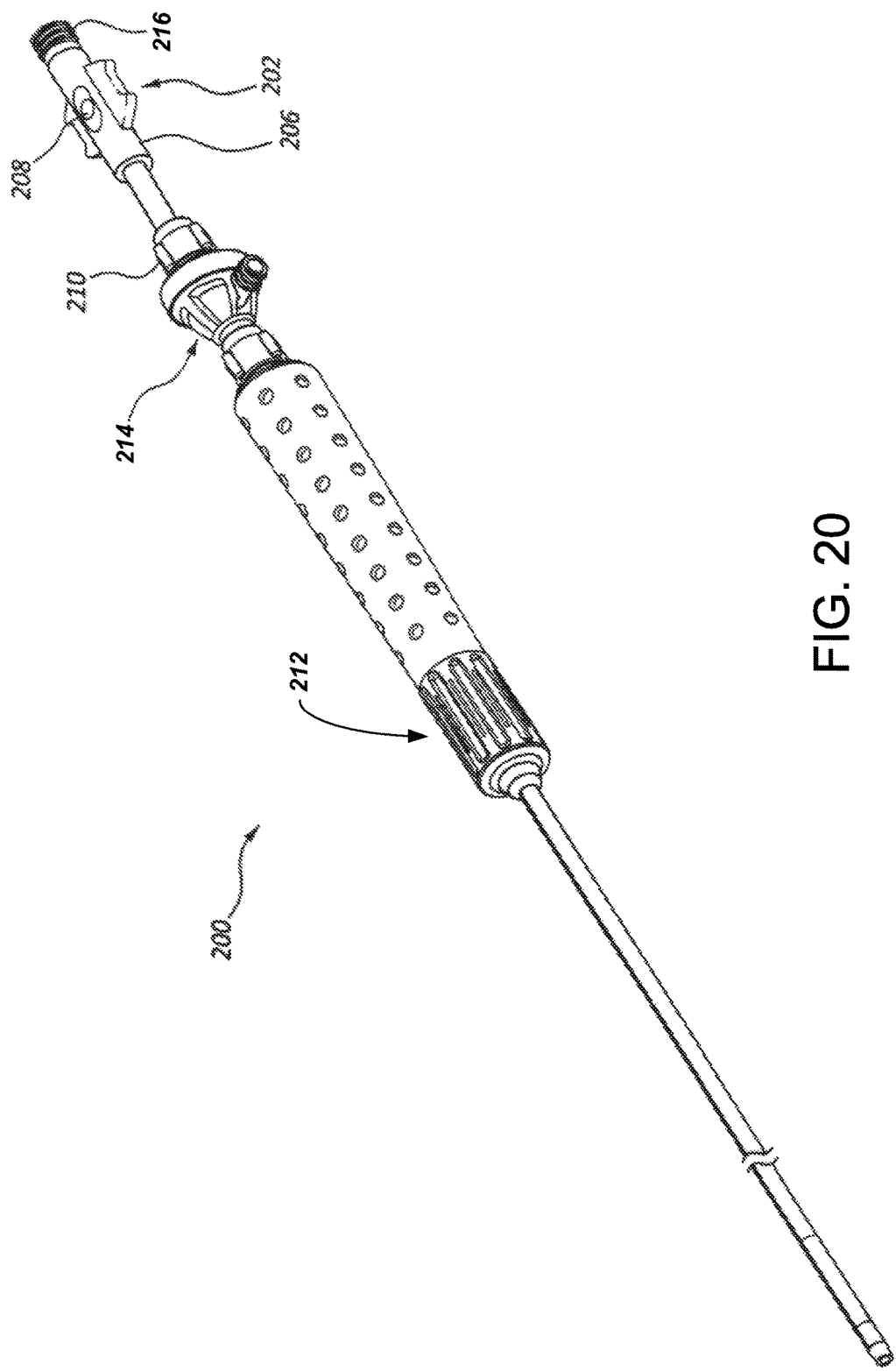
FIG. 20 is a perspective view of a sheath assembly with a flow adapter in place of an alignment device in accordance with the present disclosure.
Figure 21:
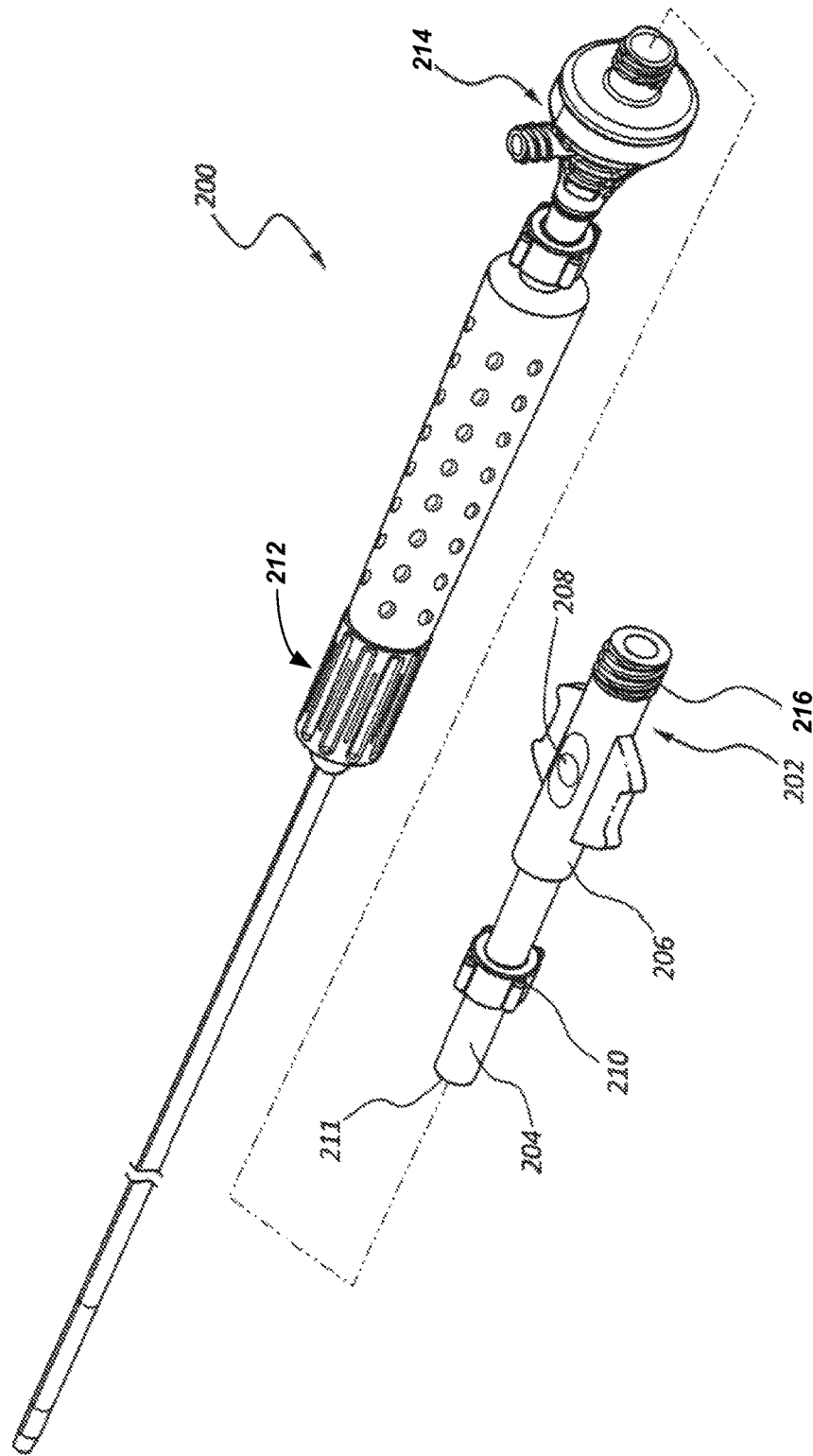
FIG. 21 is an exploded perspective view of the sheath assembly and flow adapter shown in FIG. 20.

Referring now to FIGS. 20 and 21, a separate flow adapter 202 may be coupled to valve assembly 214 of sheath assembly 200 after removing medical instrument 92A, 92B from valve assembly 214 (e.g., shown in FIGS. 15-18). Flow adapter 202 may be connected directly to valve assembly 214. As discussed above, valve assembly 214 may be integrally formed with or permanently connected to introducer 212.

Flow adapter 202 may provide a fluid-to-fluid connection across valve member 36 (not shown) of valve assembly 214. Flow adapter 202 may include insertion portion 204, hub 206, flow controller 208, and connector 210, as shown in FIG. 21. Valve insertion portion 204 may have a length sufficient to extend through and hold open valve member 36 when flow adapter 202 is assembled with valve assembly 214. Insertion portion 204 may have a length sufficient to meet with tubing of introducer 212 to provide improved advancement of the medical device through a transition between flow adapter 202 and introducer 212. When the valve assembly 214 is held in an open position by valve insertion portion 204, fluid may flow from introducer 212, through valve assembly 214, and into flow adapter 202. A medical instrument may then be inserted through introducer 212, valve assembly 214, and flow adapter 202 to a treatment site and fluid flows past valve member 36. A dilator or other medical instrument may be used to facilitate placement of flow adapter 202 and then removed once placement is achieved.

Flow adapter 202 may include flow controller 208 positioned on hub 206 to provide control of fluid flow through flow adapter 202. When flow controller 208 is in an open position, fluid may flow through valve assembly 214 and flow adapter 202. When flow controller 208 is in a closed position, fluid is stopped from flowing through flow adapter 202.

Internal lumen 211 of flow adapter 202 (see FIG. 21) may have an inner diameter that is about the same as an inner diameter of introducer 212. An outer diameter of flow adapter 202 may be the same or greater than diameter $D_1$ of opening 50 (not shown). Valve member 36 may provide at least one sealed connection point between valve assembly 214 and an outer surface of insertion portion 204 of flow adapter 202. In at least some arrangements, valve assembly 214 may provide first and second axially spaced apart sealed connection points with flow adapter 202 using valve member 36. Flow adapter 202 may be used multiple times during a procedure without affecting integrity of the valve member 36.

Connector 210 may be used to releaseably connect flow adapter 202 to valve assembly 214. Flow adapter 202 may also include connection features 216 at a proximal end thereof. Connection features 216 may provide a releasable connection to other medical instruments. Connection features 216 may include, for example, a plurality of threads, snap-fit or interference-fit connection features, or fasteners that provide the desired connection.

Alignment adapter 16 of sheath assembly 10 shown in FIG. 1 may be interposed between flow adapter 202 and valve assembly 14. In other embodiments, cap 37 of valve assembly 14 may have an elongate structure that provides an alignment function similar to alignment adapter 16. In either such embodiments, insertion portion 204 would have a length sufficient to extend through and hold open valve member 36.

One aspect of the present disclosure relates to a hemostasis valve assembly which includes a housing and a valve member. The housing includes a central bore. The valve member is positioned within the housing and includes opposed first and second primary surfaces, a thickness, an opening, and first and second slits. The valve thickness is defined between the first and second primary surfaces. The opening is formed in the first primary surface. The first and second slits intersect each other and extend through a portion of the valve thickness. At least one of the first and second slits is accessible within the opening.

The hemostasis valve assembly may further include a recess positioned between the opening and the first and second slits. The opening may have a first diameter and the recess may have a second diameter that is larger than the first diameter. The opening and recess may be arranged coaxially with an intersection point between the first and second slits. The first slit may have a length that is less than the second diameter. A size of the opening may be expandable. The first and second slits may be arranged perpendicular to each other. The second slit may have a greater length than the first slit. The hemostasis valve assembly may further include an alignment guide coupled to and extending proximally from a proximal end of the housing and having a central bore aligned coaxially with the opening and first and second slits.

Another aspect relates to a sheath assembly that includes an introducer having distal and proximal ends, a valve assembly mounted to the proximal end of the introducer, and an alignment device extending proximally from the valve assembly and having a lumen axially aligned with the valve assembly.

The alignment device may include a plurality of alignment members extending axially within the lumen. The alignment device may be releasably connected to the valve assembly. The valve assembly may include a valve member, wherein the valve member includes first and second slits intersecting at an insertion point, an opening having a first diameter, and a recess positioned between the opening and the first and second slits and having a second diameter greater than the first diameter. The lumen may be aligned with the insertion point. The lumen may have a diameter at least as great as a diameter of the opening. The valve member may have a thickness, the first slit may extend through a first portion of the thickness, and the second slit may extend through a second portion of the thickness which is different than the first portion. The valve member may include a central portion having a first thickness and a peripheral rim having a second thickness greater than the first thickness.

A further aspect relates to a sheath assembly which includes an introducer, a valve assembly, and a flow adapter. The introducer has distal and proximal ends. The valve assembly is mounted to the proximal end of the introducer. The flow adapter extends proximally from the valve assembly and includes an insertion portion extending into the valve assembly to maintain the valve assembly in an open position, and a flow controller operable to control fluid flow through the flow adapter.

The valve assembly may provide sealing engagement with the hold open portion. The flow adapter may include a flow lumen extending through the insertion portion to the flow controller. The flow adapter may include a hub to which the flow controller is mounted, wherein the insertion portion is positioned distal of the hub.

Another aspect relates to a method of manufacturing a valve member. The method includes providing a resilient valve member having a perimeter and opposing first and second primary surfaces, and forming an opening in the valve member, wherein the opening has a first diameter and a first depth extending from the first primary surface toward the second primary surface. The method also includes forming a recess in the valve member, wherein the recess is arranged coaxially with the opening and has a second diameter greater than the first diameter and a second depth extending from the opening toward the second primary surface. The method further includes forming at least one slit in the valve member, wherein the at least one slit is accessible through the opening and recess.

Forming the at least one slit may include forming first and second slits, wherein the first and second slits intersect each other. Forming the first and second slits may include arranging the first and second slits perpendicular to each other. The first slit may be formed in a bottom surface of the recess, and the second slit may be formed in the second primary surface.

Another aspect relates to a method of assembling a delivery sheath. The method includes providing an introducer, a valve assembly and an alignment member. The method further includes mounting the valve assembly to a proximal end of the introducer and mounting the alignment member to a proximal end of the valve assembly such that a lumen of the alignment member is aligned with an opening of a valve member within the valve assembly. The lumen of the alignment member is receptive of a medical instrument, the alignment member aligns the medical instrument with the opening of the valve member, and the valve member seals against an outer surface of the medical instrument at at least one location along a length of the medical instrument.

The valve member may include first and second slits intersecting at an insertion point, and the lumen is aligned with the insertion point. The valve member may further include a recess arranged coaxially and aligned with both the insertion point and the opening. The valve member may seal against an outer surface of the medical instrument at multiple spaced apart locations along the length of the medical instrument.

A further aspect relates to a method of assembling a delivery sheath. The method includes providing an introducer, a valve assembly and a flow adapter, positioning the valve assembly at a proximal end of the introducer, and mounting the flow adapter to a proximal end of the valve assembly with a portion of the flow adapter extending through a valve member of the valve assembly. The flow adapter controls fluid flow through the introducer and valve assembly.

The valve member may include at least one slit and an opening, and the valve member may provide first and second axially spaced apart sealed interfaces with the portion of the flow adapter.

As used in this specification and the appended claims, the term "engage" and "engagable" are also used broadly to mean interlock, mesh, or contact between two devices. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A hemostasis valve assembly, comprising:
 a housing; and
 a valve member positioned within the housing, the valve member comprising:
 opposed first and second primary surfaces and a valve thickness defined between the first and second primary surfaces;
 an opening formed in the first primary surface;
 first and second slits arranged intersecting each other in an axial direction along a central axis, wherein the central axis extends from the first primary surface to the second primary surface, the first and second slits extending through a portion of the valve thickness, the first slit accessible within the opening and extending from the opening through the valve thickness to a depth within the valve located a distance from the second primary surface, and the second slit accessible from the second primary surface and extending from the second primary surface through the valve thickness to a depth within the valve located a distance from a bottom surface of the opening; and a recess positioned between the opening and the first and second slits, wherein the opening has a first diameter and the recess has a second diameter, the first diameter being smaller than the second diameter.

2. The hemostasis valve assembly of claim 1, wherein the opening and recess are arranged coaxially with an intersection point between the first and second slits.

3. The hemostasis valve assembly of claim 1, wherein the first slit has a length that is less than the second diameter.

4. The hemostasis valve assembly of claim 1, wherein a size of the opening is expandable.

5. The hemostasis valve assembly of claim 1, wherein the first and second slits are arranged perpendicular to each other.

6. The hemostasis valve assembly of claim 1, wherein the second slit has a greater length than the first slit.

7. The hemostasis valve assembly of claim 1, further comprising an alignment guide coupled to and extending proximally from a proximal end of the housing and having a central bore aligned coaxially with the opening and first and second slits.

\* \* \* \* \*